(12) United States Patent
Benhida et al.

(10) Patent No.: US 9,173,892 B2
(45) Date of Patent: Nov. 3, 2015

(54) ACADESINE DERIVATIVES, PRODUCTS AND COMPOSITIONS INCLUDING SAME, THERAPEUTIC USES THEREOF, AND METHODS FOR SYNTHESIZING SAME

(75) Inventors: Rachid Benhida, Nice (FR); Patrick Auberger, Nice (FR); Vincent Malnuit, Nice (FR); Mohsine Driowya, Nice (FR); Alexandre Puissant, Nice (FR); Guillaume Robert, Nice (FR)

(73) Assignees: Universite Nice Sophia Antipolis, Nice (FR); Centre National De La Recherche Scientifique, Paris (FR); Institut National De La Sante De La Recherche Medicale, Paris (FR)

( * ) Notice: Subject to any disclaimer, the term of this patent is extended or adjusted under 35 U.S.C. 154(b) by 104 days.

(21) Appl. No.: 14/112,575

(22) PCT Filed: Apr. 17, 2012

(86) PCT No.: PCT/FR2012/000147
§ 371 (c)(1),
(2), (4) Date: Jan. 10, 2014

(87) PCT Pub. No.: WO2012/143624
PCT Pub. Date: Oct. 26, 2012

(65) Prior Publication Data
US 2014/0179626 A1  Jun. 26, 2014

(30) Foreign Application Priority Data

Apr. 18, 2011  (FR) .................................... 11 01204

(51) Int. Cl.
| | | |
|---|---|---|
| *A61K 31/70* | (2006.01) | |
| *A61K 31/7056* | (2006.01) | |
| *C07D 249/04* | (2006.01) | |
| *C07D 249/06* | (2006.01) | |
| *C07H 19/056* | (2006.01) | |
| *A61K 31/357* | (2006.01) | |
| *A61K 31/4192* | (2006.01) | |
| *A61K 31/7028* | (2006.01) | |
| *C07D 493/04* | (2006.01) | |
| *C07H 15/04* | (2006.01) | |
| *C07H 17/02* | (2006.01) | |

(52) U.S. Cl.
CPC ........... *A61K 31/7056* (2013.01); *A61K 31/357* (2013.01); *A61K 31/4192* (2013.01); *A61K 31/7028* (2013.01); *C07D 249/04* (2013.01); *C07D 249/06* (2013.01); *C07D 493/04* (2013.01); *C07H 15/04* (2013.01); *C07H 17/02* (2013.01); *C07H 19/056* (2013.01)

(58) Field of Classification Search
CPC ........... A61K 31/7056; A61K 31/4192; A61K 31/7028; C07H 17/02; C07H 15/04; C07D 249/06; C07D 493/04
See application file for complete search history.

(56) References Cited

U.S. PATENT DOCUMENTS

2011/0136754 A1*  6/2011  Peng et al. .................. 514/43

FOREIGN PATENT DOCUMENTS

| WO | 2004/022572 | 3/2004 |
|---|---|---|
| WO | 2009/060053 | 5/2009 |

OTHER PUBLICATIONS

Campàs, C. et al., "Acadesine activates AMPK and induces apoptosis in B-cell chronic lymphocytic leukemia cells but not in T lymphocytes," BLOOD, vol. 101, No. 9, pp. 3674-3680 (May 1, 2003).
Grütter, M.G., "Caspases: key players in programmed cell death," Current Opinion in Structural Biology, 10:649-655 (2000).
Jacquel, A. et al., "Apoptosis and erythroid differentiation trigged by Bcr-Abl inhibitors in CML cell lines are full distinguishable processes that exhibit different sensitivity to caspase inhibition," Oncogene (2006), pp. 1-14.
Klionsky, D.J. et al., "Guidelines for the use and interpretation of assays for monitoring autophagy in higher eukaryotes," Autophagy, 4:2, pp. 151-175 (Feb. 16, 2008).
Malnuit, V. et al., "Tandem Azide-Alkyne 1,3-Dipolar Cycloaddition/Electrophilic Addition: A Concise Three-Component Route to 4,5-Disubstituted Triazolyl-Nucleosides," Synlett, No. 13, pp. 2123-2128 (2009).
Mariño, G. et al., "Autophagy: molecular mechanisms, physiological functions and relevance in human pathology," CMLS, Cell. Mol. Life Sci., 61, pp. 1439-1454 (2004).
Robert, G. et al., "Acadesine Kills Chronic Myelogenous Leukemia (CML) Cells Through PKC-Dependent Induction of Autophagic Cell Death," PLOS ONE, vol. 4, Issue 11, e7789, 11 pages. (Nov. 2009).

* cited by examiner

*Primary Examiner* — Elli Peselev
(74) *Attorney, Agent, or Firm* — Thompson Hine LLP

(57) ABSTRACT

Acadesine derivatives as a drug, as well as the derivatives for the treatment of cancer and in particular for the treatment of chronic myeloid leukemia are described. Also, product containing the derivatives and at least one second active ingredient as a combination product for simultaneous, separate or sequential administration, in the treatment of cancer, as well as a pharmaceutical composition containing the derivatives and a pharmaceutically acceptable carrier are described. Finally, a method for inhibiting the in vitro cell proliferation including the placement of an in vitro cell in contact with the derivatives and methods for synthesis of said derivatives and methods for synthesis of the derivatives are described.

10 Claims, 9 Drawing Sheets

ACADESINE DERIVATIVES, PRODUCTS AND COMPOSITIONS INCLUDING SAME, THERAPEUTIC USES THEREOF, AND METHODS FOR SYNTHESIZING SAME

The invention relates to acadesine derivatives, also called AICAR for 5-aminoimidazole-4-carboxamide-1-β-D-ribofuranoside, in the field of drug chemistry. More specifically, the invention relates to acadesine derivatives for the treatment of cancers. Even more specifically, the invention relates to acadesine derivatives for the treatment of myeloid blood diseases such as, in particular, chronic myeloid leukemia (CML).

Malignant myeloid blood diseases are characterized by alterations in survival, proliferation or differentiation properties of myeloid-line cells. They are caused by generally acquired genetic abnormalities affecting hematopoietic stem cells or progenitors (differentiated or "engaged" stem cells) engaged in a particular differentiation pathway. These blood diseases include acute myeloblastic leukemia (AML), myelodysplastic syndromes (MDS) and myeloproliferative syndromes (MPS). Chronic myeloid leukemia (CML) is a malignant myeloproliferative syndrome (MPS) related to an abnormality in leukemic stem cells leading to an increased production of granulocytes at all differentiation stages. It is caused by an acquired cytogenetic defect resulting from the reciprocal translocation of genetic material between the long arm of chromosomes 9 and 22, the Philadelphia translocation (t9; 22) (q34-q11) or chromosome. The molecular consequence of this rearrangement is the production of a chimeric protein p210BCR-ABL in more than 95% of patients with chronic myeloid leukemia (CML).

BCR-ABL is a constitutively-activated tyrosine kinase, which explains the insensitivity of the stem cells of patients to spontaneous or induced apoptosis. These characteristics make BCR-ABL a preferred pharmacological target for therapeutic intervention in chronic myeloid leukemia (CML).

Undeniable progress has been recorded in recent years in the treatment of cancers. Treatments are provided earlier and care methods have benefitted from the provision of new pharmaceutical products that are very effective against tumors. Over just a few years, the bone marrow transplant and in particular the appearance of targeted treatments have enabled better care of patients. Indeed, one of the significant advances in recent years is the arrival on the market of imatinib mesylate (GLEEVEC® by Novartis Pharmaceuticals Corporation).

GLEEVEC®, formally imatinib mesylate (IM), a pharmacological inhibitor of BCR-ABL, c-KIT and the PDGF receptor, has thus been the treatment of reference for chronic myeloid leukemia (CML) in the past decade. It is currently the prototype of the tyrosine kinase inhibitors (TKI) used in anti-cancer therapy. However, a significant percentage of patients develop resistance to this compound and this proportion increases significantly in accelerated and acute phases of the disease. The mechanisms underlying this resistance are varied and include occasional mutations at the ATP binding site of BCR-ABL of which the mutation T315I, which generates multiple resistances and presents a real therapeutic problem, rare BCR-ABL amplifications, alterations of the signaling pathways located downstream of this kinase such as the activation of SRC kinases.

GLEEVEC® pharmacological inhibitor of BCR-ABL, c-KIT and the PDGF receptor now makes it possible to improve the prognosis of the disease and to obtain complete remissions in around 95% of cases. Chemotherapy with imatinib has thus gradually replaced transplants as the first line of treatment, and transplant indications have been reserved for patients in whom imatinib has failed.

However, as some patients do not respond to this treatment or develop resistance, particularly when the disease is in the acute transformation phase, alternative strategies to BCR-ABL inhibition and intended to block different signaling pathways downstream have been evaluated, including SRC kinase inhibition. These strategies have been found to be effective and substitution products have been evaluated, such as nilotinib, developed by the Novartis™ Pharmaceuticals Corporation or dasatinib (SPRYCEL®), developed by the Brystol-Meyers Squibb Company. SPRYCEL® dasatinib is currently prescribed to patients with resistance to GLEEVEC® pharmacological inhibitor of BCR-ABL, c-KIT and the PDGF receptor.

However, some patients, in particular those with the T315I mutation in the ATP binding site of p210BCR-ABL are refractory to almost all tyrosine kinase inhibitors (TKI) used in the treatment of chronic myeloid leukemia (CML). There is therefore a real need for alternative therapeutic strategies, in particular for patients with the T315I mutation or downstream BCR-ABL resistance.

Acadesine or 5-aminoimidazole-carboxamide riboside (AICAR) is a nucleoside with a very large number of metabolic effects. It is in particular described as an AMP-activated protein kinase (AMPK). This active principle is currently in a phase-III clinical trial for reduction of the risks of cardio or cerebrovascular complications during coronary bypass surgery. In addition, a recent study shows that this compound induces apoptosis of B cells of chronic lymphocytic leukemia (Campás et al., 2003), a blood disease for which it is in a phase-I/II study.

There is therefore a need to develop new compounds providing an alternative to the existing products or products being developed, in order to enable in particular the treatment of patients resistant to the existing therapies, in particular patients resistant to tyrosine kinase inhibitor (TKI)-type treatments. There is also a need to develop new compounds making it possible to respond to the problem of treatment exhaustion. Treatment exhaustion or tachyphylaxis refers to the slowing of the therapeutic effect after a period of use of drugs. In addition, there is also a need to develop compounds having different mechanisms of action making it possible to treat chronic myeloid leukemia and, more generally, certain cancers. Finally, there is currently a need to develop new compounds having lower cytotoxicity to the compounds currently available.

The solution to the stated problem therefore relates to compounds having the general formula:

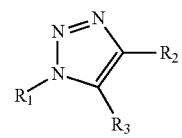

wherein:
$R_1$ is chosen from:
  a cyclic pentose group in furan form with the OH groups that are free or optionally substituted by one or more mono-, bi- or triphosphate (or prodrugs of same), acetyl, isopropylidene, benzoyl or para-toluoyl groups, a hexose group in pyran form with OH groups that are free or optionally substituted by one or more mono-, bi- or triphosphate (or prodrugs of same) or acetyl groups, a naphthyl group, optionally substituted by one or more alkyl or substituted amine groups having 1 to 4 carbon atoms, a benzyl group optionally substituted by one or more alkyl or substituted amine groups having 1 to 4 carbon atoms, phenyl, biphenyl or heteroaryl groups;

$R_2$ is chosen from:

a —$CONH_2$, —CONHMe, —CONHEt, —$CON(Me)_2$, —$CON(Et)_2$ amide group, a —$CO_2H$, $CO_2Me$, $CO_2Et$ acid or ester group, a —CN, —$C(NH_2)NH$, —C(NHMe)NH, —C(NHEt)NH cyano or amidine group, a phenyl group optionally substituted by a halogen chosen from Cl, Br, I and F, a thiophene group, a linear or branched carbon chain having 3 to 10 carbon atoms, or a methoxynaphthalene group; and $R_3$ is chosen from:

a halogen group, a furan or —CO-furan group, a thiophene or —CO-thiophene or —C≡C-thiophene group, a toluoyl group, an acetylene group, a —CO—$(CH_2)_n$—$CH_3$ group, with n between 2 and 9, a phenyl or —C≡C-phenyl group, optionally substituted by a halogen, a —C≡C—$CO_2Me$, —C≡C—$CO_2Et$, —C≡C—$CONH_2$ group, a —C≡C—$(CH_2)_6CH_3$, group, or a —C≡C-2-methoxynaphthalene group;

the racemates, enantiomers, diastereoisomers thereof and mixtures thereof, the tautomers thereof and the pharmaceutically acceptable salts thereof, as a drug.

Surprisingly, the applicant was able to demonstrate that the compounds according to the invention make it possible to reduce the viability of K562 leukemic cell lines sensitive to imatinib and/or ImaR cell lines resistant to imatinib. This is in particular demonstrated in examples 1 and 2.

In addition, the applicant was able to demonstrate that the compounds according to the invention have an action on different types of programmed cell death (PCD).

PCD plays a fundamental role in maintaining proper functioning of any living organism because it enables the cells that it no longer needs to be eliminated.

Two major types of PCD are known: PCD type-I, also called apoptosis, and PCD type-II, also called autophagy.

Caspases (cysteine proteases) are the main actors in apoptosis. They cleave various protein substrates essential for cell survival. Two major pathways lead to their activation. The intrinsic pathway is orchestrated by the proteins of the Bcl-2 family and triggered by the release of cytochrome C by the mitochondria followed by the formation of a multiprotein complex (apoptosome) at the origin of the activation of caspases 9 then 3. The extrinsic pathway is triggered at the plasma membrane by the activation of membrane receptors followed by the formation of a multiprotein complex (DISC) enabling the activation of caspases 8 then 3 (Grutter, 2000).

Autophagy can lead either to cell survival or to cell death. The initial step is the formation of double-membrane vacuoles (autophagosomes resulting from nucleation, elongation and maturation of a phagophore), which trap a portion of cytosol and the macromolecules and organites to be eliminated. The autophagosomes fuse with the lysosomes to form autophagolysosomes, in which lysosomal hydrolases (cathepsins) degrade their contents. The formation of the autophagosome is dependent on the recruitment of Atg proteins and LC3-II and p62/SQSTM1 proteins (Klionsky et al., 2008; Marino and Lopez-Otin, 2004). The mTOR pathway is involved in its regulation. In effect, activated mTOR inhibits autophagy while its inhibition by AMPK initiates this process.

As is demonstrated in example 1, the compounds according to the invention make it possible to act on the two types of programmed cell death (PCD) described above. More specifically, the mechanisms of action involved by the compounds according to the invention are autophagy or apoptosis or a combination of the two types of mechanisms. This is demonstrated in example 1.

The document entitled "Acadesine Kills Chronic Myelogenous Leukemia (CML) Cells through PKC-Dependent Induction of Autophagic Cell Death" (Robert G et al., PloS ONE, November 2009, volume 4, Issue 11) indicates in particular that acadesine is effective in the treatment of chronic myeloid leukemia (CML) and that it acts on programmed cell death type-II, i.e., an autophagy mechanism. However, this document does not disclose acadesine derivatives or the possible activity thereof in the treatment of chronic myeloid leukemia (CML).

The document entitled "Tandem Azide-Alkyne 1,3-Dipolar Cycloaddition/Electrophilic Addition: A concise Three-Component Route to 4,5-Disubstituted Triazolyl-Nucleosides" (Malnuit V et al., Synlett 2009, No. 13, pages 2123-2128) does not describe the compounds according to the invention as a drug. This document describes the synthesis of acadesine derivatives, having a general formula different from the compounds according to the invention. In addition, even if this document suggests that these compounds may have beneficial biological properties, there is nothing in this document to suggest that this type of compound can have an indication as a drug, and, more specifically, in the treatment of cancer, such as, for example, chronic myeloid leukemia (CML).

The present invention also relates, secondly, to a product containing a compound according to the invention and at least one second active agent as a combination product for simultaneous, separate or sequential administration in the treatment of cancer.

It also relates, thirdly, to a pharmaceutical composition including a compound according to the invention and a pharmaceutically acceptable carrier.

It relates, fourthly, to a method for inhibiting in vitro cell proliferation including placing an in vitro cell in contact with a compound according to the invention.

Finally, it relates, fifthly, to methods for synthesis of the compounds according to the invention.

According to the invention, the different compounds described above can in particular be synthesized according to the different methods described below. In these methods, the groups $R_1$, $R_2$ and $R_3$ are as defined above.

According to a first alternative, the compounds of the invention are obtained by a one-pot reaction, in which an azide ($R_1N_3$) reacts with an alkyne ($R_2$—C≡C—H) and an electrophile ($R_3$—X, for which X=Br or I) in the presence of copper (catalyst) to lead to trisubstituted triazole products, according to the following reaction scheme:

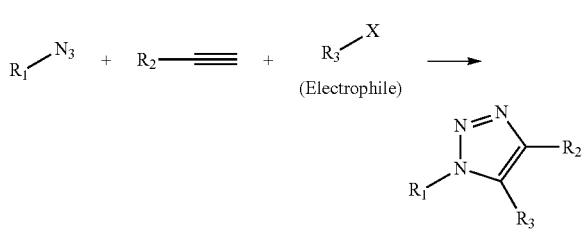

According to a second alternative, the compounds according to the invention are obtained by a Sonogashira reaction, in which triazole substrates (X=Br or I) are reacted in the presence of alkynes ($R_4$—C≡C—H) and a palladium catalyst, such as, for example $Pd(PPh_3)_4$ or $Pd(PPh_3)_2Cl_2$). This reaction makes it possible to obtain 1,4,5-trisubstituted 1,2,3-triazole derivatives (containing $R_1$, $R_2$ and a $R_4$—C≡C— group in position 5 falling under the definition of $R_3$ provided above, for which $R_4$=H, $SiMe_3$, Ph, $CO_2Me$, $Co_2Et$), according to the following reaction scheme:

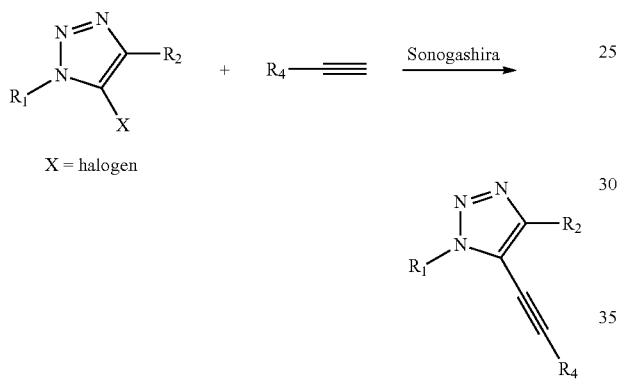

According to a third alternative, the compounds according to the invention are obtained by a Stille (or Suzuki-Miyaura)-type palladium coupling reaction. This reaction makes it possible to couple a stannic derivative ($R_3$—$SnBu_3$) or a boronic acid derivative ($R_3$—$B(OH)_2$) with a 1,4-trisubstituted 5-halo-triazole (X=Br or I) in order to obtain 1,4,5-trisubstituted 1,2,3-triazoles containing, in position 5, an $R_3$ group (aryl or heteroaryl), according to the following reaction scheme:

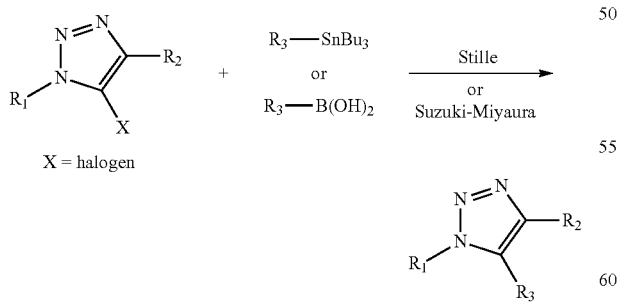

According to a fourth alternative, the compounds according to the invention are obtained by a reaction between an azide ($R_1N_3$) and an alkyne ($R_2$—C≡C—H) in the presence of a copper-based catalyst and an oxidant (such as, for example, $H_2O_2$). This reaction enables the synthesis of 1,4,5-trisubstituted 1,2,3-trizoles (containing $R_1$, $R_2$ and the group $R_2$—C≡C— in position 5 falling under the definition of $R_3$ specified above), according to the following reaction scheme:

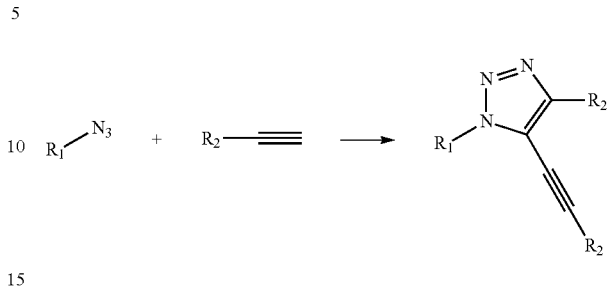

The invention will be better understood upon reading the following non-limiting description, with reference to the appended drawings, wherein.

Figure 1:
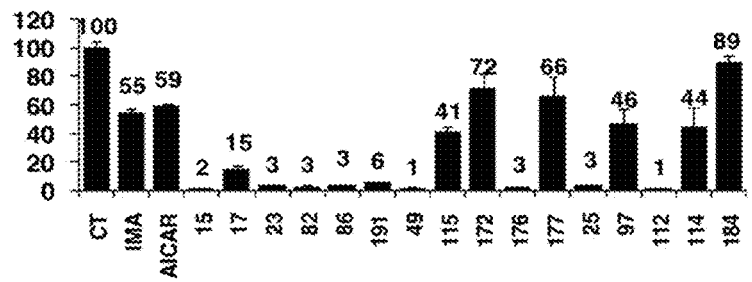
FIGS. 1 to 20 show the results of studies intended to screen compounds according to the invention in order to determine their efficacy and the general mechanisms of action of certain of these compounds.

The compounds according to the invention are compounds with the general formula:

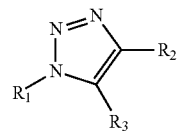

wherein:
$R_1$ is chosen from:
 a cyclic pentose group in furan form with the OH groups that are free or optionally substituted by one or more mono-, bi- or triphosphate (or prodrugs of same), acetyl, isopropylidene, benzoyl or para-toluoyl groups,
 a hexose group in pyran form with OH groups that are free or optionally substituted by one or more mono-, bi- or triphosphate (or prodrugs of same) or acetyl groups,
 a naphthyl group, optionally substituted by one or more alkyl or substituted amine groups having 1 to 4 carbon atoms,
 a benzyl group optionally substituted by one or more alkyl or substituted amine groups having 1 to 4 carbon atoms,
 phenyl, biphenyl or heteroaryl groups;
$R_2$ is chosen from:
 a —$CONH_2$, —CONHMe, —CONHEt, —$CON(Me)_2$, —$CON(Et)_2$ amide group,
 a —$CO_2H$, $CO_2Me$, $CO_2Et$ acid or ester group, a —CN, —$C(NH_2)NH$, —C(NHMe)NH, —C(NHEt)NH cyano or amidine group,
 a phenyl group optionally substituted by a halogen chosen from Cl, Br, I and F,
 a thiophene group,
 a linear or branched carbon chain having 3 to 10 carbon atoms, or
 a methoxynaphthalene group; and $R_3$ is chosen from:
- a halogen group,
- a furan or —CO-furan group,
- a thiophene or —CO-thiophene or —C≡C-thiophene group,
- a toluoyl group,
- an acetylene group,
- a —CO—(CH$_2$)$_n$—CH$_3$ group, with n between 2 and 9,
- a phenyl or —C≡C-phenyl group, optionally substituted by a halogen,
- a —C≡C—CO$_2$Me, —C≡C—CO$_2$Et, —C≡C—CONH$_2$ group,
- a —C≡C—(CH$_2$)$_6$CH$_3$, group, or
- a —C≡C—2-methoxynaphthalene group;

the racemates, enantiomers, diastereoisomers thereof and mixtures thereof, the tautomers thereof and the pharmaceutically acceptable salts thereof, as a drug.

The pharmaceutically acceptable salts are addition salts with inorganic acids such as hydrochloride, hydrobromide, hydroiodide, sulfate, phosphate, diphosphate and nitrate or with organic acids such as acetate, maleate, fumarate, tartrate, succinate, citrate, lactate, methanesulfonate, p-toluene-sulfonate, pamoate and stearate. Also covered by the present invention, when they can be used, are the salts formed from bases such as sodium or potassium hydroxide.

Preferably, the compounds according to the invention are compounds with the general formula:

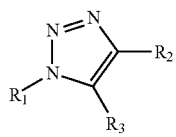

wherein:

$R_1$ is chosen from:

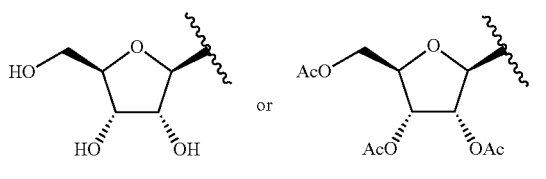

β-D-Ribose tri-O-acetyl-β-D-Ribose

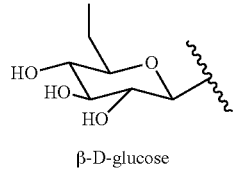

β-D-glucose tetra-O-acetyl-β-D-glucose

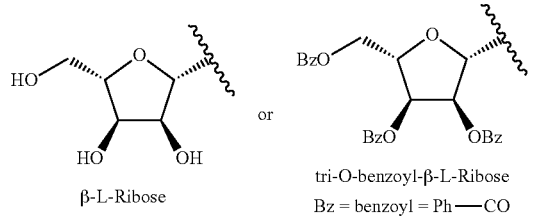

β-L-Ribose tri-O-benzoyl-β-L-Ribose
Bz = benzoyl = Ph—CO

-continued

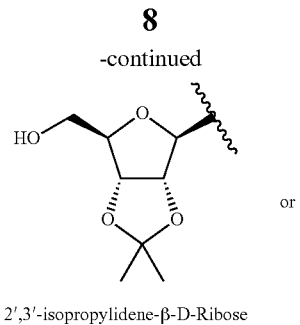

2′,3′-isopropylidene-β-D-Ribose

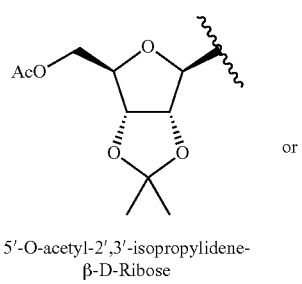

5′-O-acetyl-2′,3′-isopropylidene-β-D-Ribose

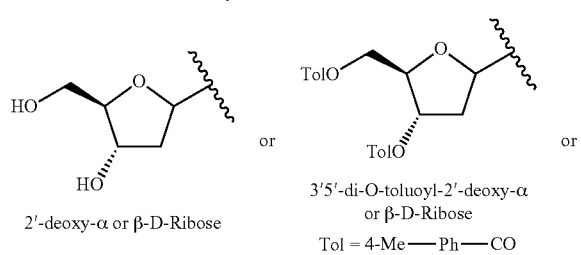

2′-deoxy-α or β-D-Ribose

3′5′-di-O-toluoyl-2′-deoxy-α or β-D-Ribose

Tol = 4-Me—Ph—CO

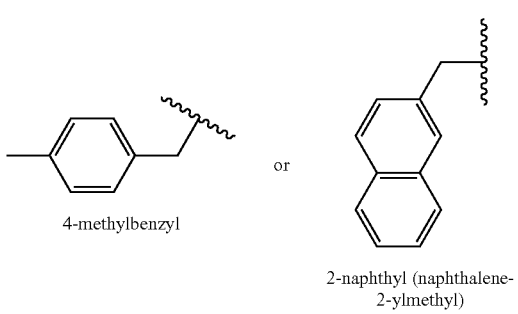

4-methylbenzyl 2-naphthyl (naphthalene-2-ylmethyl)

$R_2$ is chosen from —CONH$_2$, —CO$_2$Me, —CO$_2$Et, phenyl, thiophene, —(CH$_2$)$_6$CH$_3$, p-fluoro-phenyl or 2-methoxynaphthalene; and $R_3$ is chosen from I, Cl, furan, CO-furan, CO-thiophene, acetylene, CO—(CH$_2$)$_5$—CH$_3$, toluoyl, —C≡C—CO$_2$Et, thiophene, phenyl, —C≡C-phenyl, —C≡C-thiophene, —C≡C—(CH$_2$)$_6$CH$_3$, —C≡C-(p-fluoro-phenyl), or —C≡C—2-methoxynaphthalene;

the racemates, enantiomers, diastereoisomers thereof and mixtures thereof, the tautomers thereof and the pharmaceutically acceptable salts thereof, as a drug.

Also preferably, the compounds according to the invention are compounds with the general formula:

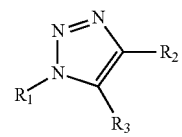

wherein $R_1$ is:

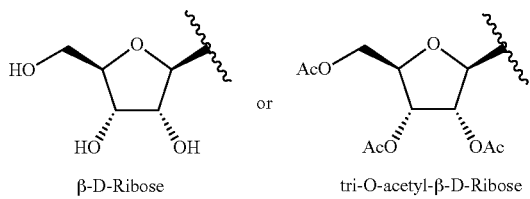

β-D-Ribose tri-O-acetyl-β-D-Ribose

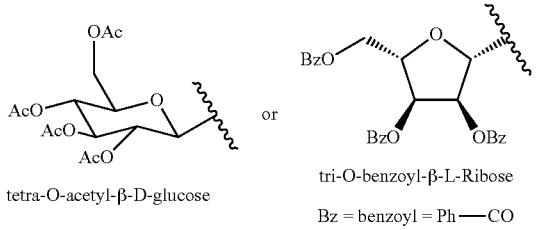

tetra-O-acetyl-β-D-glucose tri-O-benzoyl-β-L-Ribose

Bz = benzoyl = Ph—CO

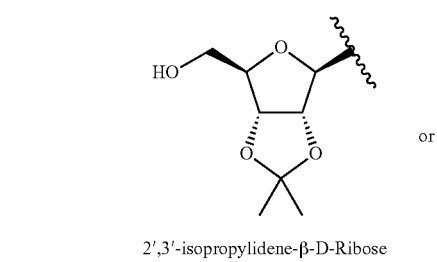

2',3'-isopropylidene-β-D-Ribose

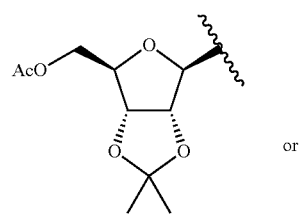

5'-O-acetyl-2',3'-isopropylidene-β-D-Ribose

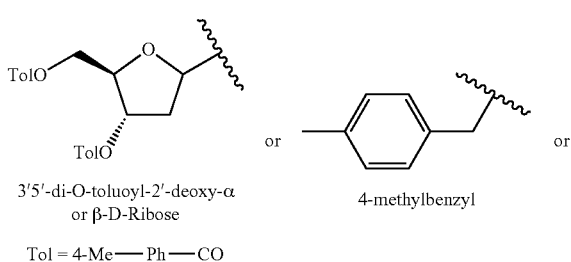

3'5'-di-O-toluoyl-2'-deoxy-α or β-D-Ribose 4-methylbenzyl

Tol = 4-Me—Ph—CO

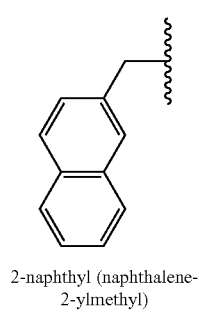

2-naphthyl (naphthalene-2-ylmethyl)

and when $R_1$ is a β-D-ribose, then:
$R_2$=CONH$_2$ and $R_3$=I, Cl, CO-Furan, CO-thiophene, toluoyl or acetylene;
or
$R_2$=CO$_2$Me and $R_3$=I, furan or acetylene;
or
$R_2$=phenyl and $R_3$=I;
when $R_1$ is a tri-O-acetyl-β-D-ribose group, then:
$R_2$=CO$_2$Et and $R_3$=Cl, CO—(CH$_2$)$_5$—CH$_3$, CO-furan, toluoyl, —C≡C—CO$_2$Et, thiophene or phenyl;
or
$R_2$=phenyl and $R_3$=—C≡C-phenyl;
or
$R_2$=thiophene and $R_3$=—C≡C-thiophene;
or
$R_2$=(CH$_2$)$_6$CH$_3$ and $R_3$=—C≡C—(CH$_2$)$_6$CH$_3$;
or
$R_2$=p-fluoro-phenyl and $R_3$=—C≡C-p-fluoro-phenyl;
or
$R_2$=2-methoxynaphthalene and
$R_3$=—C≡C—2-methoxynaphthalene;
when $R_1$ is a tetra-O-acetyl-β-D-glucose group, then $R_2$=CO$_2$Et and $R_3$=I or —C≡C—CO$_2$Et;
when $R_1$ is a tri-O-benzoyl-β-L-ribose group, then $R_2$=CO$_2$Et and $R_3$=—C≡C—CO$_2$Et;
when $R_1$ is a 2',3'-isopropylidene-β-D-ribose group, then $R_2$=CO$_2$Et and $R_3$=—C≡C—CO$_2$Et or thiophene;
when $R_1$=5'-O-acetyl-2',3'-isopropylidene-β-D-ribose, then $R_2$=CO$_2$Et and $R_3$=—C≡C—CO$_2$Et or thiophene;
when $R_1$ is a 3',5'-di-O-toluoyl-2'-deoxy-β-D-ribose group, then $R_2$=CO$_2$Et and $R_3$=—C≡C—CO$_2$Et;
when $R_1$ is a 4-methylbenzyl group, then:
$R_2$=CO$_2$Et and $R_3$=—C≡C—CO$_2$Et;
or
$R_2$=phenyl and $R_3$=—C≡C-phenyl;
when $R_1$ is a 2-naphthyl (naphthalene-2-ylmethyl) group, then:
$R_2$=CO$_2$Et and $R_3$=I;
or
$R_2$=CO$_2$Et and $R_3$=—C≡C—CO$_2$Et;
or
$R_2$=Phenyl and $R_3$=—C≡C-phenyl;
the racemates, enantiomers, diastereoisomers thereof and mixtures thereof, the tautomers thereof and the pharmaceutically acceptable salts thereof, as a drug.

Also preferably, the compounds according to the invention are compounds with the general formula:

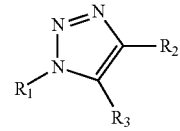

wherein $R_1$ is:

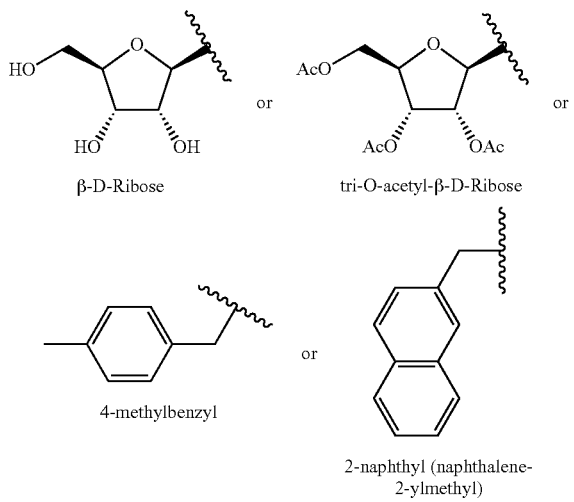

β-D-Ribose    tri-O-acetyl-β-D-Ribose 4-methylbenzyl    2-naphthyl (naphthalene-2-ylmethyl)

and
when $R_1$ is a β-D-ribose group, then:
$R_2$=CONH$_2$ and $R_3$=Cl, CO-furan, CO-thiophene or toluoyl;
or
$R_2$=CO$_2$Me and $R_3$=I or acetylene;
or
$R_2$=phenyl and $R_3$=I;
when $R_1$ is a tri-O-acetyl-β-D-ribose group, then:
$R_2$=CO$_2$Et and $R_3$=CO—(CH$_2$)$_5$—CH$_3$, CO-furan, toluoyl, —C≡C—CO$_2$Et, thiophene or phenyl;
or
$R_2$=phenyl and $R_3$=—C≡C-phenyl;
or
$R_2$=thiophene and $R_3$=—C≡C-thiophene;
or
$R_2$=(CH$_2$)$_6$CH$_3$ and $R_3$=—C≡C—(CH$_2$)$_6$CH$_3$;
or
$R_2$=p-fluoro-phenyl and $R_3$=—C≡C-p-fluoro-phenyl;
or
$R_2$=2-methoxynaphthalene and
$R_3$=—C≡C—2-methoxynaphthalene;
when $R_1$ is a 4-methylbenzyl group, then:
$R_2$=CO$_2$Et and $R_3$=—C≡C—CO$_2$Et;
or
$R_2$=phenyl and $R_3$=—C≡C-phenyl;
when $R_1$ is a 2-naphthyl (naphthalene-2-yl-methyl) group, then:
$R_2$=CO$_2$Et and $R_3$=I;
or
$R_2$=CO$_2$Et and $R_3$=—C≡C—CO$_2$Et;
or
$R_2$=Phenyl and $R_3$=—C≡C-phenyl;
the racemates, enantiomers, diastereoisomers thereof and mixtures thereof, the tautomers thereof and the pharmaceutically acceptable salts thereof, as a drug.

As non-limiting examples of preferred compounds according to the invention, it is possible to cite the compounds:
1'-(4-ethoxycarbonyl-5-iodo-[1,2,3]-triazol-1-yl)-2',3',5'-tri-O-acetyl-β-D-ribofuranose;
1'-(4-carbamoyl-5-iodo-[1,2,3]-triazol-1-yl)-β-D-ribofuranose;
1'-(4-methoxycarbonyl-5-ethynyl-[1,2,3]-triazol-1-yl)-β-D-ribofuranose;
1-(naphthyl-2-methyl)-4-ethoxycarbonyl-5-iodo-1,2,3-triazole;
1-(naphthyl-2-methyl)-4-ethoxycarbonyl-5-ethyl propiolate-1,2,3-triazole;
1'-(4-ethoxycarbonyl-5-ethyl propiolate-[1,2,3]-triazol-1-yl)-2',3',5'-tri-O-acetyl-β-D-ribofuranose;
1'-(4-ethoxycarbonyl-5-(2-thienyl)-[1,2,3]-triazol-1-yl)-2',3',5'-tri-O-acetyl-β-D-ribofuranose;
1'-(4-ethoxycarbonyl-5-phenyl-[1,2,3]-triazol-1-yl)-2',3',5'-tri-O-acetyl-β-ribofuranose;
1-(4-methylbenzyl)-4-ethoxycarbonyl-5-ethyl propiolate-1,2,3-triazole;
1'-(4-heptyl-5-(non-1-yn-1-yl-[1,2,3]-triazol-1-yl)-2',3',5'-tri-O-acetyl-β-D-ribofuranose;
1'-(4-ethoxycarbonyl-5-ethyl propiolate-[1,2,3]-triazol-1-yl)-2',3',5'-tri-O-benzoyl-β-L-ribofuranose;
2'-deoxy-1'-(4-ethoxycarbonyl-5-ethyl propiolate-[1,2,3]-triazol-1-yl)-3',5'-di-O-(p-toluoyl)-α-D-ribofuranose;
1'-(4-ethoxycarbonyl-5-ethyl propiolate-[1,2,3]-triazol-1-yl)-2',3',4',6'-tetra-O-acetyl-β-D-glucopyranose;
1'-(4-ethoxycarbonyl-5-ethyl propiolate-[1,2,3]-triazol-1-yl)-2',3'-O-isopropylidene-β-D-ribofuranose;
1'-(4-ethoxycarbonyl-5-ethyl propiolate-[1,2,3]-triazol-1-yl)-2',3'-O-isopropylidene-5'-O-acetyl-β-D-ribofuranose;
1'-(4-ethoxycarbonyl-5-(2-thienyl)-[1,2,3]-triazol-1-yl)-2',3'-O-isopropylidene-β-D-ribofuranose; and
1'-(4-ethoxycarbonyl-5-(2-thienyl)-[1,2,3]-triazol-1-yl)-2',3'-O-isopropylidene-5'-O-acetyl-β-D-ribofuranose.

Particularly advantageously, the compounds according to the invention are chosen from:
1'-(4-ethoxycarbonyl-5-(2-thienyl)-[1,2,3]-triazol-1-yl)-2',3',5'-tri-O-acetyl-β-D-ribofuranose;
1'-(4-ethoxycarbonyl-5-ethyl propiolate-[1,2,3]-triazol-1-yl)-2',3',5'-tri-O-acetyl-β-D-ribofuranose;
1'-(4-ethoxycarbonyl-5-ethyl propiolate-[1,2,3]-triazol-1-yl)-2',3'-O-isopropylidene-β-D-ribofuranose;
1'-(4-ethoxycarbonyl-5-ethyl propiolate-[1,2,3]-triazol-1-yl)-2',3'-O-isopropylidene-5'-O-acetyl-β-D-ribofuranose; and
1-(4-methylbenzyl)-4-ethoxycarbonyl-5-ethyl propiolate-1,2,3-triazole.

Even more preferably, the compounds according to the invention are chosen from:
1'-(4-ethoxycarbonyl-5-(2-thienyl)-[1,2,3]-triazol-1-yl)-2',3',5'-tri-O-acetyl-β-D-ribofuranose
1'-(4-ethoxycarbonyl-5-phenyl-[1,2,3]-triazol-1-yl)-2',3',5'-tri-O-acetyl-β-D-ribofuranose
1-(4-methylbenzyl)-4-ethoxycarbonyl-5-ethyl propiolate-1,2,3-triazole
1'-(4-ethoxycarbonyl-5-ethyl propiolate-[1,2,3]-triazol-1-yl)-2',3',4',6'-tetra-O-acetyl-β-D-glucopyranose
1'-(4-ethoxycarbonyl-5-(2-thienyl)-[1,2,3]-triazol-1-yl)-2',3'-O-isopropylidene-β-D-ribofuranose.

According to the invention, the compounds can also be in the form of prodrugs. The term prodrug refers to a pharmacological substance (a drug) that is administered in an inactive form (or in a form much less active than its metabolite). Once administered, the prodrug is metabolized in vivo into an active metabolite. More specifically, prodrugs can be classified into two categories based on their sites of conversion into their definitive active form.

Type I prodrugs are those in which the conversion is intracellular. Type II prodrugs are those that are converted extracellularly, in particular in the digestive fluids or the systemic circulation.

The two types can be further subdivided into subtype A or B, based on additional criteria. Those of type IA and IB are distinguished by the activation site, which is the site where therapeutic action occurs or does not occur. For type IIA and IIB, they are classified according to whether the conversion has taken place in the gastrointestinal tract or the systemic circulation.

Advantageously, the compounds according to the invention can include groups making it possible to increase their solubility, their cellular penetration and their bioavailability.

As non-limiting examples of prodrugs, it is possible to cite:
prodrugs containing groups $R_5$, $R_6$ or $R_7$ or a combination thereof of the amino acid or analog, sulfate or phosphonium type with the following general formula:

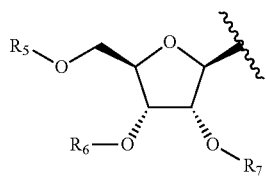

wherein:
$R_5$ is preferably an amino acid, sulfonium or phosphonium;
$R_6$ and $R_7$ are preferably identical or different amino acids such as glycine, valine or leucine;
phosphate or monophosphate prodrugs such as phosphoramidates containing $R_8$ and $R_9$ groups, or a combination thereof of the amino acid or analog, alcohol, or sulfur type with the general formula:

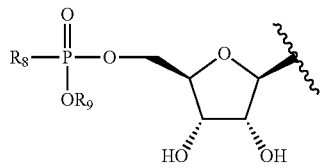

wherein:
$R_8$ is preferably an amino acid such as alanine, leucine or valine or amine analogs;
$R_9$ is a phenyl or a phenyl analog such as $CH_3Ph$ or $CH_3OPh$.

As is demonstrated in example 1, the compounds according to the invention make it possible to act on the two types of programmed cell death (PCD) described above. Among the signaling pathways used by the compounds according to the invention, it appears that certain compounds enable inhibition of the mTOR pathway.

The mTOR protein is at the center of numerous metabolic processes, such as, in particular, protein synthesis, G1 progression, cell survival or the cytoskeleton. Therefore, the signaling pathway passing through this protein is currently considered to be a new therapeutic target of great interest in the treatment of numerous cancers and metabolic diseases.

As non-limiting examples of metabolic diseases for which the compounds according to the invention appear to be suitable, it is possible to cite diabetes, solid tumors, in particular carcinomas of all origins including, for example, tumors of the colon, the breast, the prostate and melanomas.

Preferably, the compounds according to the invention are suitable of cancer treatments, i.e., for applications in oncology and/or hematology-oncology.

As non-limiting examples of treatments for which the compounds are suitable, it is possible to cite the treatment of malignant blood diseases such as chronic leukemia (CML, CLL), acute myeloblastic leukemias (AML), high-risk myelodysplastic syndromes (MDS), multiple myeloma, the treatment of resistance to imatinib and to the second-generation tyrosine kinase inhibitors in the case of CML and Vidaza (5-Aza) in the case of myelodysplastic syndromes (MDS). The compounds according to the invention also have applications in the treatment of epithelial cancers and metabolic diseases. They can also be used to circumvent resistance to other drugs, in particular GLEEVEC® pharmacological inhibitor of BCR-ABL, c-KIT and the PDGF receptor.

Specifically, the compounds according to the invention are suitable for the treatment of:
adults and children with newly diagnosed Philadelphia chromosome (bcr-abl)-positive (Ph+) chronic myeloid leukemia (CML) when the bone marrow graft cannot be envisaged as a first-line treatment;
adults and children with chronic-phase Ph+CML after failure of the alpha interferon treatment, or in an accelerated phase or in blast crisis;
adult patients with newly diagnosed Philadelphia chromosome-positive acute lymphoid leukemia (PH+ALL) in association with chemotherapy;
adult patients with refractory Ph+ALL or in single-therapy relapse;
adult patients with myelodysplastic/myeloproliferative syndromes (MDS/MPS) associated with rearrangements of the PDGFR (platelet-derived growth factor receptor) gene;
adult patients with an advanced-stage hypereosinophilic syndrome (HES) and/or chronic eosinophilic leukemia (CEL) associated with a rearrangement of the FIP1L1-PDGFRα;
adult patients with Kit (CD117)-positive inoperable and/or metastatic malignant gastrointestinal stromal tumors (GIST);
adult patients with a significant risk of relapse after removal of a GIST Kit (CD117)-positive gastrointestinal stromal tumor. Patients with a low or very low risk should not be treated; and
adult patients with inoperable dermatofibrosarcoma protuberans (DFSP or Darier-Ferr and disease) and adult patients with DFSP in relapse and/or metastatic not controlled by surgical treatment.

Advantageously, the compounds according to the invention are particularly suitable for the treatment of cancers, in particular cancers resistant to tyrosine kinase inhibitors (TKI).

Particularly advantageously, the compounds according to the invention are particularly suitable for the treatment of chronic myeloid leukemia (CML), in particular CML resistant to tyrosine kinase inhibitors (TKI) such as, for example, imatinib, dasatinib and nilotinib commonly used in the treatment of this pathology.

The invention also relates to a product containing a compound according to the invention and at least one second active ingredient as a combination product for simultaneous, separate or sequential administration, in the treatment of cancer.

Advantageously, the second active principle is an antitumor agent, an anti-inflammatory agent or an agent reducing the side effects related to the compounds according to the invention.

Preferably, the second active ingredient is an antitumor compound chosen from the alkylating agents, the antimetabolites, the vegetable alkaloids, the topoisomerase inhibitors and the antitumor antibiotics.

As non-limiting examples of an antitumor agent that can be used according to the invention, it is possible to cite in particular bortezomib, cisplatin, carboplatin, ifosfamide, chlorambucil, busulfan, thiotepa, 5-fluorouracil (5FU), fludarabine, methotrexate, vincristine, vinblastine, vinorelbine, paclitaxel, docetaxel, derivatives of camptothecin, amsacrine, anthracyclines, derivatives of epipodophyllotoxin, doxorubicin, daunorubicin, actinomycin D, mitomycin C, plicamycin and bleomycin. It is also possible to cite the TKI's used in different tumor pathologies such as, for example, imatinib, dasatinib, nilotinib and sunitinib. Alternatively, the combination product according to the invention includes an association of a compound according to the invention and at least two other antitumor agents, or at least three other antitumor agents or more.

The term simultaneous therapeutic use, as used in the present invention, refers to an administration of at least two active principles by the same route and at the same or substantially the same time.

The term separate therapeutic use, as used in the present invention, refers to an administration of at least two active principles at the same or substantially the same time by different routes.

The term sequential therapeutic use, as used in the present invention, refers to an administration of at least two active principles at different times, with the route of administration being identical or different.

More specifically, this refers to a mode of administration according to which the entire administration of one of the active principles is performed before the administration of the other(s) begins.

It is thus possible to administer one of the active principles for several months before administering the other active principle(s). There is no simultaneous treatment in this case. It is also possible to envisage an alternating administration of each active principle for several weeks.

The invention also relates to a pharmaceutical composition including a compound according to the invention and a pharmaceutically acceptable carrier.

The route of administration of the composition according to the invention can be oral, parenteral, topical or ocular. Preferably, the pharmaceutical composition is packaged in a form suitable for oral use.

Thus, by the oral route, the composition may be in the form of tablets, capsules, sugar-coated tablets, syrups, suspensions, solutions, powders, granules, emulsions, suspensions of microbeads or nanobeads or lipid or polymer vesicles enabling controlled release.

Alternatively, when the composition according to the invention is administered by the parenteral route, it can be in the form of solutions or suspensions for perfusion or for intramuscular, intravenous or subcutaneous injection.

Also alternatively, when the composition according to the invention is administered topically, the pharmaceutical composition according to the invention is more specifically intended for the treatment of the skin and mucous membranes and can be in liquid, pasty or solid form, and more specifically in the form of ointments, aqueous, hydroalcoholic or oily solutions, dispersions of the lotion type, aqueous, anhydrous or lipophilic gels, powders, soaked pads, syndets, wipes, foams, sticks, shampoos, compresses, cleansing bases, emulsions with a liquid or semi-liquid consistency of the milk type, obtained by dispersion of a fatty phase in an aqueous phase (O/W) or the reverse (W/O), or suspensions or emulsions with a soft, semi-liquid or solid consistency of the cream, gel or pomade type. It can also be in the form of suspensions of microbeads or nanobeads or lipid or polymer vesicles or polymer or gel patches enabling controlled release.

After performing stability and solubility studies, it appears that the compounds according to the invention are particularly stable and soluble in solutions including:

DMA (dimethylacetamide);

Tween 60 Polysorbate 60 (polyoxyethylene (20) sorbitan monostearate) or Tween 80 (polyoxyethylene (20) sorbitan monooleate); and PBS (phosphate-buffered saline) or water ($H_2O$).

Preferably, the compounds according to the invention are solubilized in a composition including:

2% DMA (dimethylacetamide) by total weight of the composition;

5% Tween 80 (polyoxyethylene (20) sorbitan monooleate) by total weight of the composition; and 93% PBS (phosphate-buffered saline) by total weight of the composition.

According to the invention, the subject to be treated is preferably a mammal. More preferably, it is a human being, a horse, a dog or a cat. Even more preferably, the patient to be treated is a human being.

The invention also relates to a method for inhibiting in vitro cell proliferation including the placement of an in vitro cell in contact with a compound according to the invention.

Finally, the invention relates to methods for synthesis of the compounds according to the invention.

According to a first embodiment, the compounds according to the invention can be synthesized according to a method including the steps of:

a one-pot reaction of an azide of formula $R_1N_3$ with an alkyne of formula $R_2$—C≡C—H and an electrophile $R_3$—X, X being chosen from Cl, Br or I in the presence of a copper catalyst; and obtaining 1,4,5-trisubstituted 1,2,3-triazole compounds, according to the following reaction scheme:

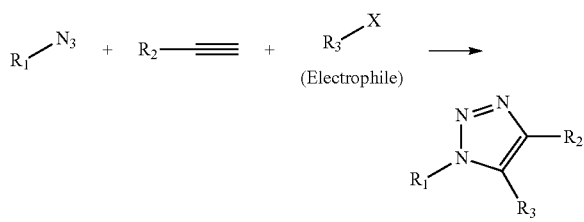

According to a second embodiment, the compounds according to the invention can be synthesized according to a method including the steps of:

a Sonogashira reaction, in which triazole substrates (for which X is chosen from Br or I) are reacted in the presence of alkynes of formula $R_4$—C≡C—H and a palladium catalyst; and obtaining 1,4,5-trisubstituted 1,2,3-triazole derivatives, for which $R_3$ in position 5 corresponds to the $R_4$—C≡C- group, and $R_4$ is chosen from H, $SiMe_3$, Ph, $CO_2Me$ and $Co_2Et$, according to the following reaction scheme:

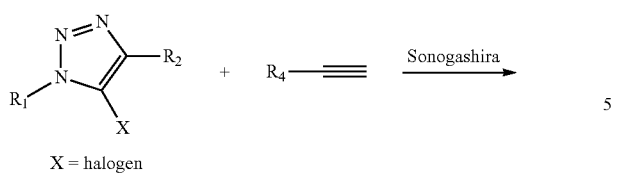

X = halogen

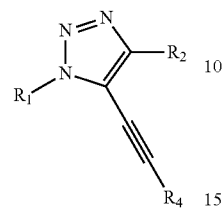

According to a third embodiment, the compounds according to the invention can be synthesized according to a method including the steps of:
- a Stille or Suzuki-Miyaura-type palladium coupling reaction of a stannic derivative of formula $R_3$—$SnBu_3$ or a boronic acid derivative of formula $R_3$—$B(OH)_2$ with a 1,4-trisubstituted 5-halo-triazole, for which X is chosen from Br or I; and
- obtaining 1,4,5-trisubstituted 1,2,3-trizoles containing, in position 5, an $R_3$ group of the aryl or heteroaryl type, according to the following reaction scheme:

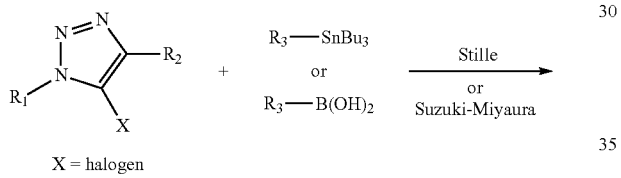

X = halogen

According to a fourth embodiment, the compounds according to the invention can be synthesized according to a method including the steps of:
- reacting an azide of formula $R_1N_3$ with an alkyne of formula $R_2$—C≡C—H in the presence of a copper-based catalyst and an oxidant; and
- obtaining 1,4,5-trisubstituted 1,2,3-trizoles for which $R_3$ in position 5 corresponds to the group $R_2$—C≡C—, according to the following reaction scheme:

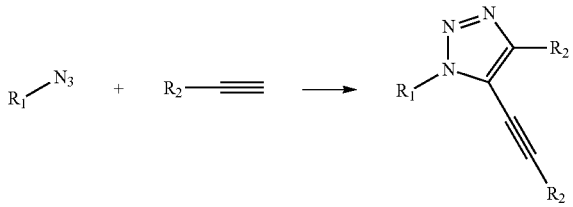

EXAMPLES

Example 1

Sixteen new compounds, analogs of AICAR (acadesine), were evaluated on two types of chronic myeloid leukemia (CML) lines: sensitive (K562) or resistant (ImaR) to imatinib. These are the 16 compounds presented in table 1 below.

TABLE 1

| Molecule code | Chemical formula of the molecule | Chemical name of the molecule |
| --- | --- | --- |
| 15 | | 1'-(4-ethoxycarbonyl-5-chloro-[1,2,3]-triazol-1-yl)-2',3',5'-tri-O-acetyl-β-D-ribofuranose |
| 17 | | 1'-(4-carbamoyl-5-iodo-[1,2,3]-triazol-1-yl)-β-D-ribofuranose |
| 23 | | 1-(naphthyl-2-methyl)-4-ethoxycarbonyl-5-iodo-1,2,3-triazole |

TABLE 1-continued

| Molecule code | Chemical formula of the molecule | Chemical name of the molecule |
|---|---|---|
| 82 | | 1'-(4-ethoxycarbonyl-5-(2-thienyl)-[1,2,3]-triazol-1-yl)-2',3',5'-tri-O-acetyl-β-D-ribofuranose |
| 86 | | 1'-(4-ethoxycarbonyl-5-phenyl-[1,2,3]-triazol-1-yl)-2',3',5'-tri-O-acetyl-β-D-ribofuranose |
| 191 | | 1'-(4-ethoxycarbonyl-5-iodo-[1,2,3]-triazol-1-yl)-2',3',4',6'-tetra-O-acetyl-β-D-glucopyranose |
| 49 | | 1'-(4-ethoxycarbonyl-5-ethyl propiolate-[1,2,3]-triazol-1-yl)-2',3',5'-tri-O-acetyl-β-D-ribofuranose |
| 115 | | 1'-(4-phenyl-5-phenylacetylene-[1,2,3]-triazol-1-yl)-2',3',5'-tri-O-acetyl-β-D-ribofuranose |
| 172 | | 1'-(4-(3-thienyl)-5-(3-ethynylthiophene)-[1,2,3]-triazol-1-yl)-2',3',5'-tri-O-acetyl-β-D-ribofuranose |
| 176 | | 1'-(4-heptyl-5-(non-1-yn-1-yl)-[1,2,3]-triazol-1-yl)-2',3',5'-tri-O-acetyl-β-D-ribofuranose |

TABLE 1-continued

| Molecule code | Chemical formula of the molecule | Chemical name of the molecule |
|---|---|---|
| 177 | | 1'-(4-(4-fluorophenyl)-5-(4-fluorophenylacetylene)-[1,2,3]-triazol-1-yl)-2',3',5'-tri-O-acetyl-β-D-ribofuranose |
| 25 | | 1-(naphthyl-2-methyl)-4-ethoxycarbonyl-5-ethyl propiolate-1,2,3-triazole |
| 97 | | 1-(naphthyl-2-methyl)-4-phenyl-5-phenylacetylene-1,2,3-triazole |
| 112 | | 1-(4-methylbenzyl)-4-ethoxycarbonyl-5-ethyl propiolate-1,2,3-triazole |
| 114 | | 1-(4-methylbenzyl)-4-phenyl-5-phenylacetylene-1,2,3-triazole |

TABLE 1-continued

| Molecule code | Chemical formula of the molecule | Chemical name of the molecule |
| --- | --- | --- |
| 184 | | 1'-(4-(6-methoxynaphth-2-yl)-5-((6-methoxynaphth-2-yl)acetylene)-[1,2,3]-triazol-1-yl)-2',3',5'-tri-O-acetyl-β-D-ribofuranose |

The K562 leukemic cell line is obtained from the pleural effusion of a patient with CML. This line is a good model for studying this disease. The imatinib-resistant ImaR cells are generated from K562 cells by exposure to increasing doses of imatinib. The K562 and ImaR cells are cultivated at 37° C. under 5% $CO_2$ in an RPMI 1640 medium containing 5% fetal bovine serum and supplemented with sodium pyruvate and antibiotics (penicillin-streptomycin).

a. Screening of the 16 Compounds by Measuring the Cell Viability

To screen the 16 compounds according to the invention, the metabolic activity of the K562 and ImaR cells is studied after 24 or 48 hours of treatment with 0.5 mM (effective dose of AICAR) of these different compounds. FIGS. 1 to 4 reflect the study of the cell viability.

FIG. 1 shows the percentage of imatinib-sensitive K562 cells (K562) that are viable after stimulation or not for 24 hours with imatinib (1 μM), AICAR or one of the 16 different compounds according to the invention (0.5 mM) described in table 1 above in a 96-well plate. After the addition of XTT reagent, the absorbance is measured at 490 nm.

Figure 2:
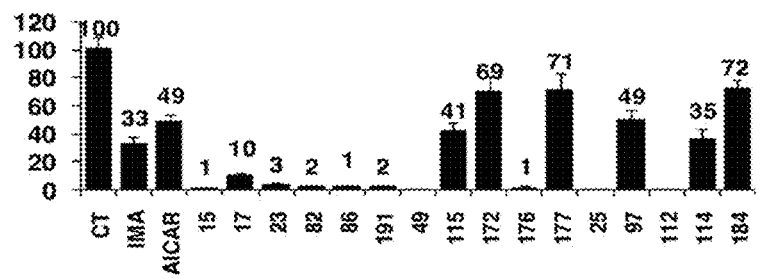

FIG. 2 shows the percentage of imatinib-sensitive K562 cells (K562) that are viable after stimulation or not for 48 hours with imatinib (1 μM), AICAR or one of the 16 different compounds according to the invention (0.5 mM) described in table 1 above in a 96-well plate. After the addition of XTT reagent, the absorbance is measured at 490 nm.

Figure 3:
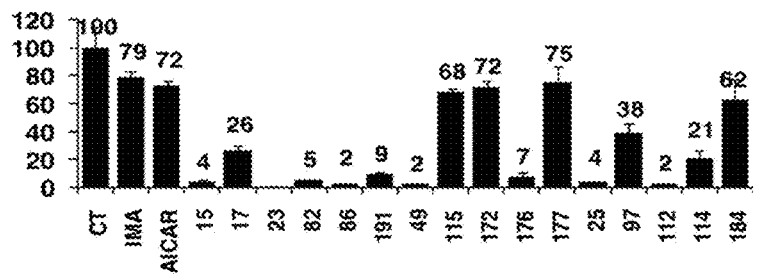

FIG. 3 shows the percentage of imatinib-resistant cells (ImaR) that are viable after stimulation or not for 24 hours with imatinib (1 μM), AICAR or one of the 16 different compounds according to the invention (0.5 mM) described in table 1 above in a 96-well plate. After the addition of XTT reagent, the absorbance is measured at 490 nm.

Figure 4:
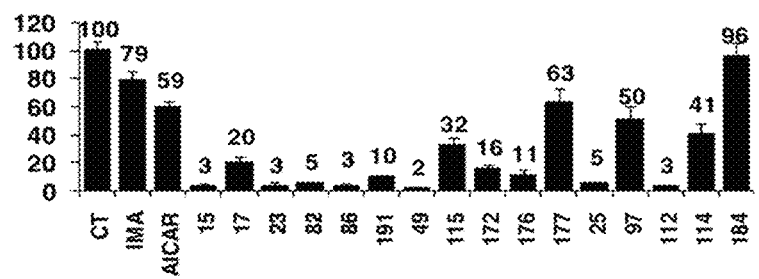

FIG. 4 shows the percentage of imatinib-resistant cells (ImaR) that are viable after stimulation or not for 48 hours with imatinib (1 μM), AICAR or one of the 16 different compounds according to the invention (0.5 mM) described in table 1 above in a 96-well plate. After the addition of XTT reagent, the absorbance is measured at 490 nm.

The results obtained show that all of the 16 compounds induce, after 24 or 48 hours of stimulation, a reduction in the cell viability in the two types of clones. This reduction in cell viability is greater than the positive control. It is also greater than or comparable to the imatinib or AICAR compounds. Thus, these 16 compounds appear to be interesting candidates for active principles intended for the treatment of CML.

In addition, among these 16 compounds, 9 compounds (15, 23, 82, 86, 191, 49, 176, 25, 112) induce, after 24 or 48 hours of stimulation, and practically identically in the two types of clones, a significant reduction in cell viability. Indeed, the percentage of viable cells changes, after 24 hours of treatment, to values below 10%. Moreover, and as expected, imatinib induces, in the K562 line, a cell viability loss of more than 50% after 48 hours of stimulation, whereas for the ImaR line, the cell viability is affected only slightly.

Figure 5:
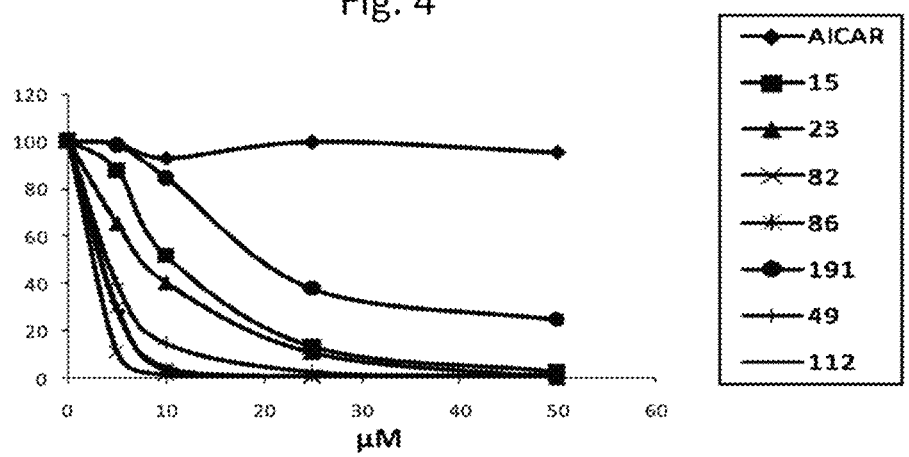

AICAR, by contrast, leads to a cell viability loss regardless of the clone considered (FIGS. 1A, 1B). Seven preferred compounds are then used in dose-response experiments (concentrations increasing from 5 to 50 μM for 24 or 48 hours of treatment) on the two types of clones (FIGS. 1 to 4).

b. Dose-Response Experiment of 7 Compounds:

FIG. 5 shows a dose-response experiment on K562 cells exposed for 24 hours to imatinib (1 μM) (for a complete dose-response of the effects of imatinib on K562S and K562R cells, see Jacquele et al., Oncogene 2007, 26, 2445-2458) at increasing doses (5, 10, 25 and 50 μM) of AICAR or of one of the 7 compounds chosen from compounds 15, 23, 82, 86, 191, 49 and 112.

Figure 6:
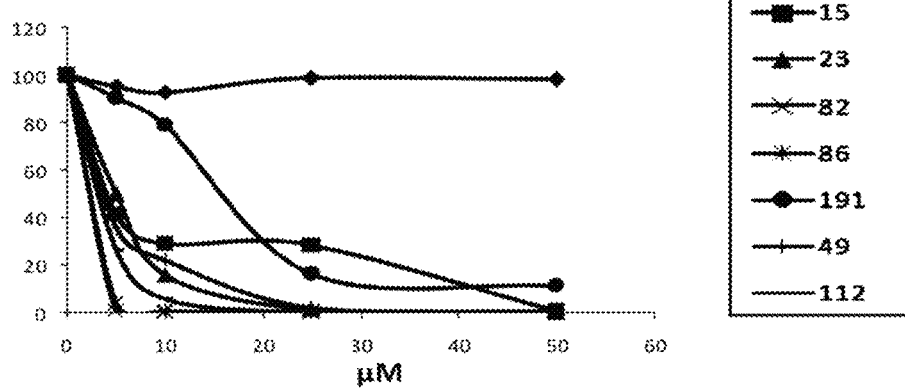

FIG. 6 shows a dose-response experiment on K562 cells exposed for 48 hours to imatinib (1 μM) (for a complete dose-response of the effects of imatinib on K562S and K562R cells, see Jacquele et al., Oncogene 2007, 26, 2445-2458) at increasing doses (5, 10, 25 and 50 μM) of AICAR or of one of the 7 compounds chosen from compounds 15, 23, 82, 86, 191, 49 and 112.

Figure 7:
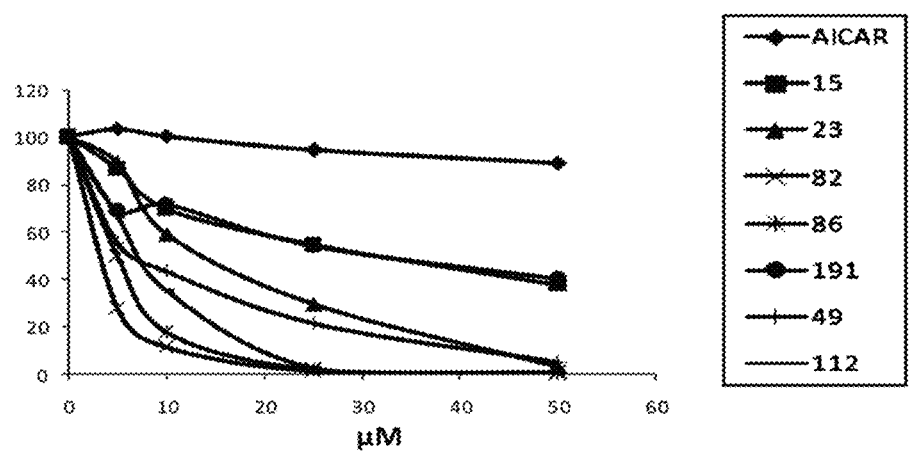

FIG. 7 shows a dose-response experiment on ImaR cells exposed for 24 hours to imatinib (1 μM) (for a complete dose-response of the effects of imatinib on K562S and K562R cells, see Jacquele et al., Oncogene 2007, 26, 2445-2458) at increasing doses (5, 10, 25 and 50 μM) of AICAR or of one of the 7 compounds chosen from compounds 15, 23, 82, 86, 191, 49 and 112.

Figure 8:
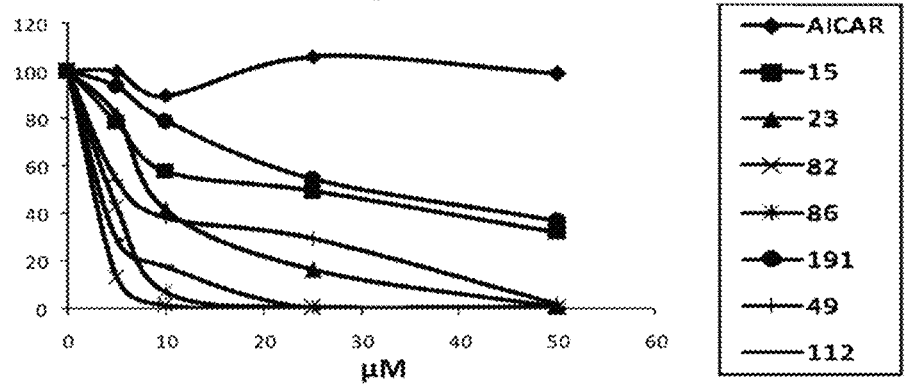

FIG. 8 shows a dose-response experiment on ImaR cells exposed for 48 hours to imatinib (1 μM) (for a complete dose-response of the effects of imatinib on K562S and K562R cells, see Jacquele et al., Oncogene 2007, 26, 2445-2458) at increasing doses (5, 10, 25 and 50 μM) of AICAR or of one of the 7 compounds chosen from compounds 15, 23, 82, 86, 191, 49 and 112.

The curves of FIGS. 5 to 8 show the dose-response effect of these 7 compounds. AICAR, ineffective at these concentrations, serves as a reference. After the addition of XTT reagent, the absorbance is measured at 490 nm.

The results shown in FIGS. 5 to 8 show a dose-dependent reduction in the number of viable cells for the 7 compounds after 24 hours of stimulation. These 7 compounds are found to be particularly effective on the two lines at concentrations as low as 5 µM (15, 23, 82, 86, 191, 49, 112). The IC50 is around 2.5 µM for compounds 82, 86 and 112 and around 10 µM for compounds 15, 23, 191 and 49. By comparison, AICAR, at these same concentrations, is ineffective. Finally, the K562 clone appears to be slightly more sensitive to these compounds than the ImaR clone.

c. Flow Cytometry Analysis of the Cell Cycle:

The percentage of cells in each of the phases of the cell cycle (subG1, cells in apoptosis, G0/G1, S and G2/M, FIG. 3A) is determined by flow cytometry, after incubation of the two cell lines with imatinib, AICAR or compounds 82, 86, 112, 15, 23, 191 and 49.

Figure 9:
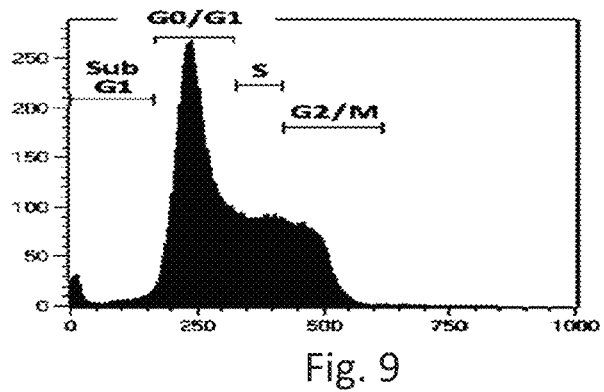

FIG. 9 shows a cell distribution model of the cells in each of the phases of the cell cycle (subG1, G0/G1, S, G2/M). The x-axis of the graph of FIG. 9 corresponds to the quantity of DNA marked with propidium iodide while the y-axis corresponds to the number of cells.

Figure 10:
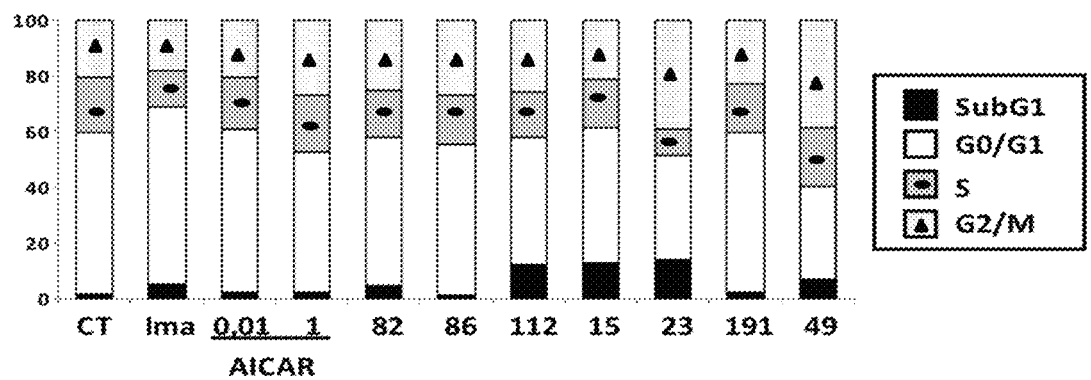

FIG. 10 shows the percentage of cells in each of the phases of the cell cycle (y-axis) when K562 cells are stimulated for 24 hours with imatinib (3 µM), AICAR (0.01 mM and 1 mM), with compounds 82 (2.5 µM), 86 (2.5 µM), 112 (2.5 µM) or with compounds 15 (10 µM), 23 (10 µM), 191 (10 µM) and 49 (10 µM). The nuclei are marked with propidium iodide, then the proportion of cells in the different phases of the cell cycle (subG1, G0/G1, S, G2/M) is determined.

Figure 11:
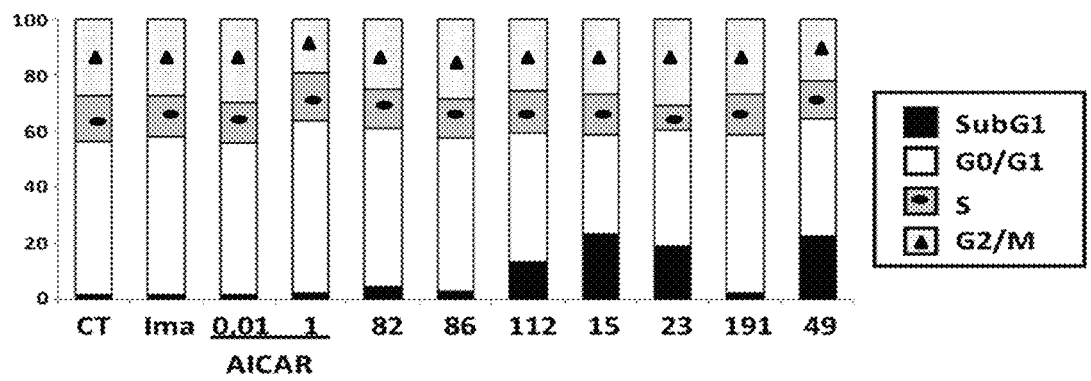

FIG. 11 shows the percentage of cells in each of the phases of the cell cycle (y-axis) when ImaR cells are stimulated for 24 hours with imatinib (3 µM), AICAR (0.01 mM and 1 mM), with compounds 82 (2.5 µM), 86 (2.5 µM), 112 (2.5 µM) or with compounds 15 (10 µM), 23 (10 µM), 191 (10 µM) and 49 (10 µM). The nucleii are marked with propidium iodide, then the proportion of cells in the different phases of the cell cycle (subG1, G0/G1, S, G2/M) is determined.

The results shown in FIGS. 10 and 11 show an increase in the percentage of cells in phase G0/G1 of the cell cycle after 24 hours of treatment with imatinib. A small fraction of cells is also accumulated in stage subG1, suggesting an apoptosis phenomenon. As expected, these effects are not observed in the ImaR clone. With regard to AICAR, it appears to cause the cell cycle to stop in G2/M for the K562 clone and in G0/G1 for the ImaR cells. Finally 5 of the 7 compounds (82, 86, 15, 23, 49) induce an increase in the proportion of K562 and ImaR cells in the G2/M phase, accompanied, for compounds 112, 15, 23 and 49, by a very pronounced accumulation of cells in the subG1 phase and a reduction in the number of cells in G0/G1.

Figure 12:
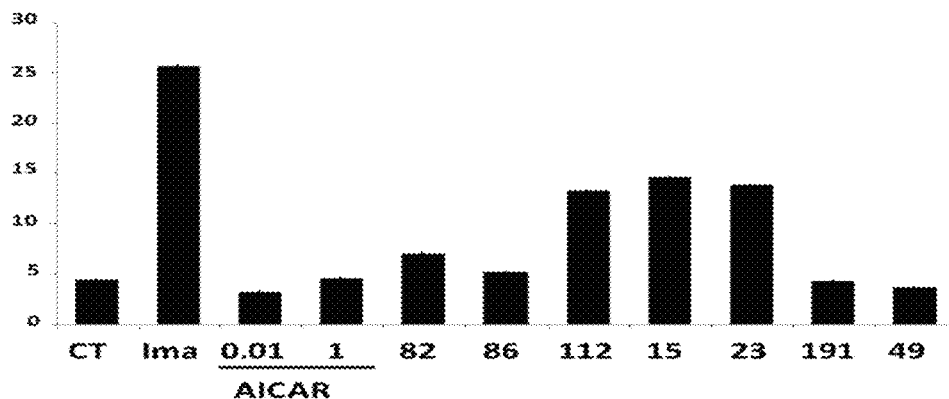

The compounds induce the stopping of the K562S and K562R cells in phase G2/M of the cell cycle that may or may not be accompanied by cell apoptosis.

d. Analysis of the Activation of Caspases 3, 8 and 9 in the K562 and ImaR Cells:

i) Measurement of the Caspase-3 Activity:

FIG. 12 shows the caspase-3 activity in U/mg of protein (y-axis) when imatinib-sensitive K562 cells are stimulated for 24 hours with imatinib (3 µM), AICAR (0.01 mM and 1 mM), compounds 82 (2.5 µM), 86 (2.5 µM), 112 (2.5 µM) or with compounds 15 (10 µM), 23 (10 µM), 191 (10 µM) and 49 (10 µM). The cells are lyzed and 10 µg of proteins are placed in the presence of Ac-DEVD-AMC in a 96-well plate. The fluorescence emission at 460 nm resulting from the release of AMC is then recorded.

Figure 13:
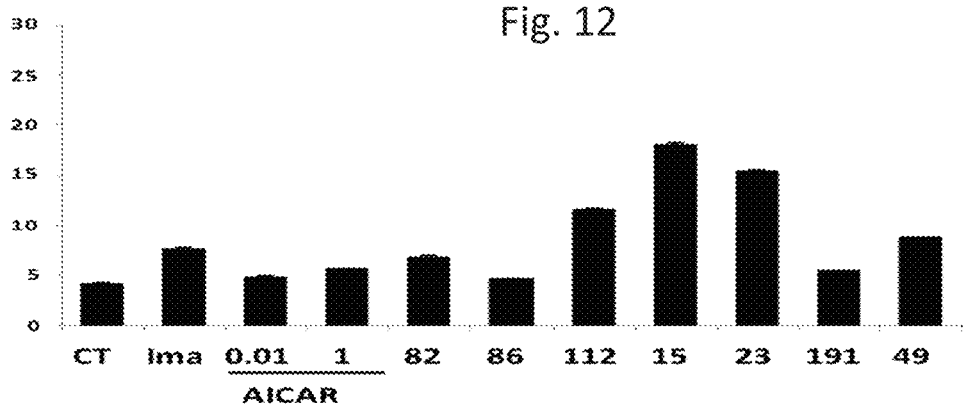

FIG. 13 shows the caspase-3 activity in U/mg of protein (y-axis) when imatinib-resistant ImaR cells are stimulated for 24 hours with imatinib (3 µM), AICAR (0.01 mM and 1 mM), compounds 82 (2.5 µM), 86 (2.5 µM), 112 (2.5 µM) or with compounds 15 (10 µM), 23 (10 µM), 191 (10 µM) and 49 (10 µM). The cells are lyzed and 10 µg of proteins are placed in the presence of Ac-DEVD-AMC in a 96-well plate. The fluorescence emission at 460 nm resulting from the release of AMC is then recorded.

The results of these FIGS. 12 and 13 show that the treatment of K562 cells with 3 µM of imatinib for 24 hours induces practically no increase in the caspase-3 activity in the ImaR cells, while it is increased by a factor of around 4 in the K562 cells. AICAR (1 mM), by contrast, is incapable of inducing this activation regardless of the clone considered. These results confirm the effects observed in the analysis of the cell cycle by flow cytometry: compounds 112, 15 and 23 induce an increase in the caspase-3 activity by a factor ranging from 2 to 3 with respect to the control in the K562 and ImaR cells. Interestingly, compound 49 induces an increase in the caspase-3 activity in the ImaR clone but not in the K562 cells.

Figure 14:
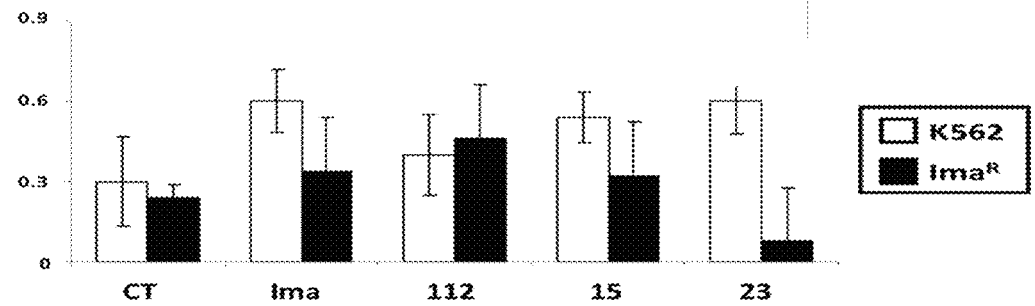

These results lead to the measurement of the activation of caspases 8 and 9 for these three compounds 112, 15 and 23.

ii) Measurement of the Caspase-8 and 9 Activities:

FIG. 14 shows the caspase-8 activity in U/mg of protein (y-axis) when imatinib-sensitive K562 cells (white bars) or imatinib-resistant ImaR cells (black bars) are stimulated for 24 hours with imatinib (3 µM), with compounds 112 (2.5 µM), 15 (10 µM) or 23 (10 µM). The cells are lyzed and the caspase-8 activities are measured using 10 µg of proteins and Ac-IETD-AMC. The fluorescence emission at 460 nm resulting from the release of AMC is then recorded.

Figure 15:
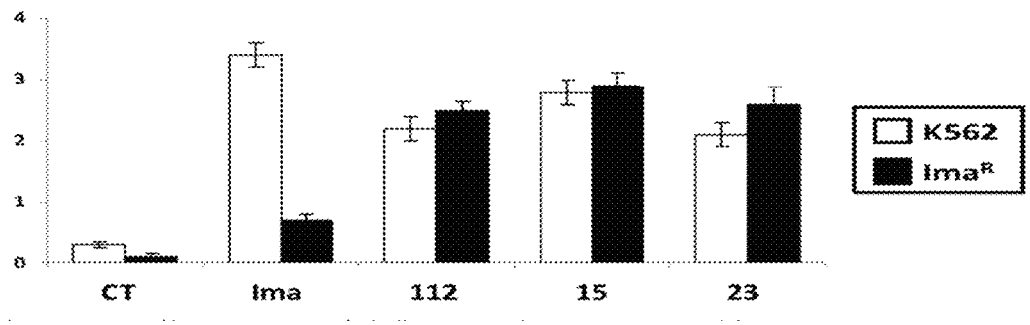

FIG. 15 shows the caspase-9 activity in U/mg of protein (y-axis) when imatinib-sensitive K562 cells (white bars) or imatinib-resistant ImaR cells (black bars) are stimulated for 24 hours with imatinib (3 µM), with compounds 112 (2.5 µM), 15 (10 µM) or 23 (10 µM). The cells are lyzed and the caspase-9 activities are measured using 10 µg of proteins and Ac-LEHD-AMC. The fluorescence emission at 460 nm resulting from the release of AMC is then recorded.

Figure 16:
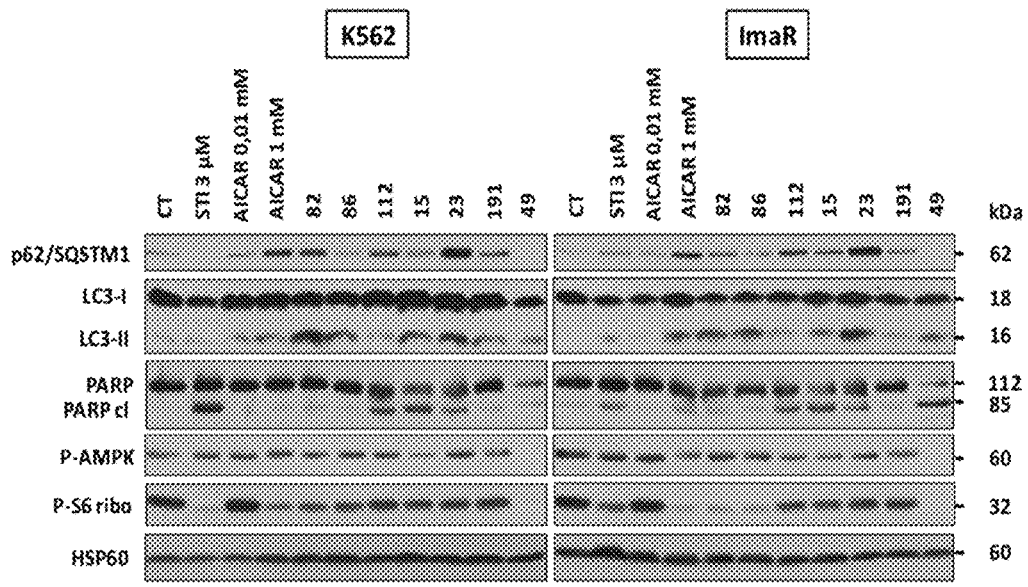

The results shown in FIGS. 14 and 15 show that no significant induction in the caspase-8 activity is measured in the presence of the different compounds (FIG. 14). By contrast, the treatment of K562 cells with imatinib induces a strong increase in the caspase-9 activity, which is not the case in the ImaR cells. Compounds 112, 15 and 23 also induce, very similarly in the two types of clones, the activation of this caspase (FIG. 15).

e. Analysis of the Expression and Phosphorylation of Specific Apoptosis and Autophagy Markers and the State of Activation of the mTOR Pathway:

i) Analysis of the Expression and Phosphorylation of Specific Apoptosis and Autophagy Markers:

FIG. 16 shows a western blot analysis of the expression and phosphorylation of specific apoptosis and autophagy markers. The K562 and ImaR cells are stimulated for 24 hours with imatinib (3 µM), AICAR (0.01 mM and 1 mM), compounds 82 (2.5 µM), 86 (2.5 µM), 112 (2.5 µM) or compounds 15 (10 µM), 23 (10 µM), 191 (10 µM) and 49 (10 µM). The cells are lyzed and 35 µg of proteins are separated by SDS-PAGE (12 or 14% polyacrylamide gel) and analyzed by western blot with antibodies specific to each of the markers.

The results of the western blot presented in FIG. 16 make it possible to distinguish the type of programmed cell death (PCD) involved in the cytotoxicity of compounds 82, 86, 112, 15, 23, 191 and 49, the expression and phosphorylation of specific markers of apoptosis and autophagy. The results obtained show an increase in the expression of p62/SQSTM1, occurring in the early stages of autophagy, in the K562 and ImaR cells treated by AICAR (1 mM) and compounds 82, 86, 112, 15, 23 and 191. During the autophagy, LC3-I is cleaved into LC3-II, then this form binds with phosphatidylethanolamine in order to be inserted into the membrane of the phagophore and enable the elongation of the autophagosome. This aggregation of LC3-I into LC3-II, shown by western blot, therefore represents an excellent means of demonstrating an induction of autophagy. LC3 is cleaved into the two types of clones in the presence of AICAR (1 mM) or compounds 82, 86, 15, 23, 191 and 49. In addition, during apoptosis, a certain number of proteins are cleaved by the caspases. Among them, PARP is the main substrate of caspase-3. In both types of clones exposed to imatinib or to compounds 112, 15, 23 and 49, the appearance of the characteristic cleavage fragment at 85 kDa (PARP cl) is observed. These observations therefore confirm the results above.

Finally, to determine the involvement of the AMPK/mTOR pathway in the initiation of the autophagic process, the level of phosphorylation of P-AMPK, the AMPK protein (shown by delayed gel migration) and P—S6 ribo, the ribosomal protein S6, an indirect substrate of mTOR were shown. Interestingly, it is noted that AMPK is activated in the presence of 1 mM of AICAR and different compounds of interest. This activation is correlated with an inhibition of the mTOR pathway shown by massive dephosphorylation of the ribosomal protein S6.

To confirm that the mTOR pathway is inhibited in the presence of the different compounds, the phosphorylation of a direct substrate of mTOR was performed: protein 4E-BP1.

ii) Analysis of the State of Activation of the mTOR Pathway

Figure 17:
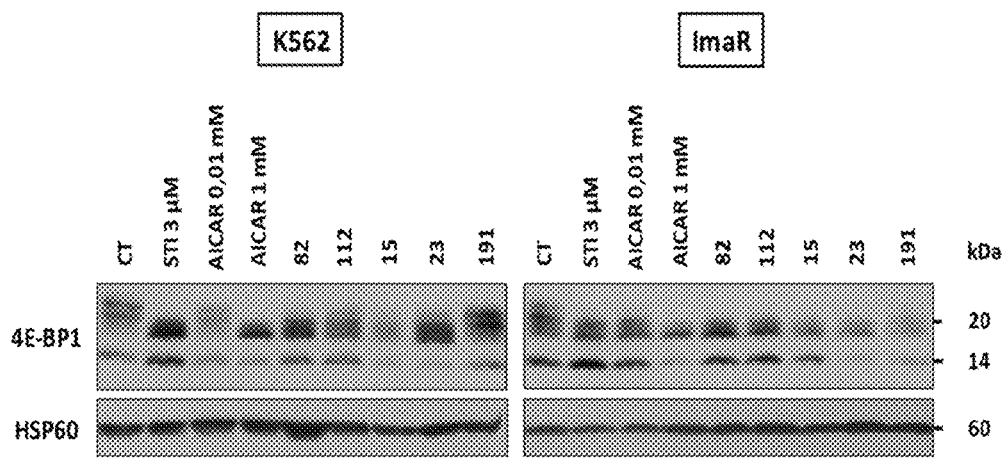

FIG. 17 shows a western blot analysis of the state of activation of the mTOR pathway by studying the phosphorylation of 4E-BP1, which is a direct substrate of mTOR. The K562 and ImaR cells are stimulated for 24 hours with imatinib (3 µM), AICAR (0.01 mM and 1 mM), compounds 82 (2.5 µM), 112 (2.5 µM) or compounds 15 (10 µM), 23 (10 µM) and 191 (10 µM). The cells are lyzed and 30 µg of proteins are separated by SDS-PAGE (13% polyacrylamide gel) and analyzed by western blot with an antibody specific to the 4E-BP1 protein. The delayed gel migration observed reflects the level of phosphorylation of 4E-BP1.

Figure 18:
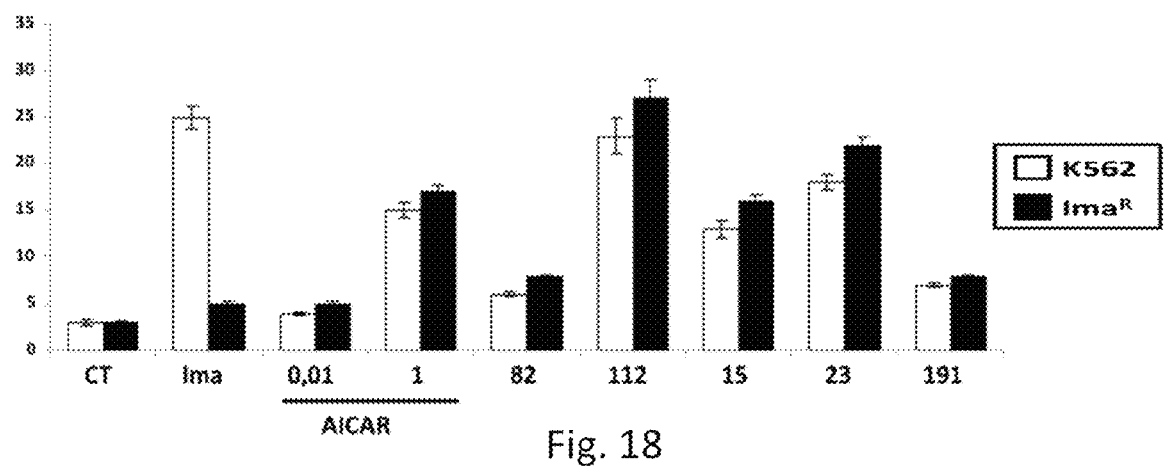

The western blot shows delayed gel migration that is more or less pronounced according to its degree of phosphorylation. Thus, a total reduction in the phosphorylation of 4E-BP1 in the two sensitive and resistant clones treated with AICAR (1 mM) and with compounds 82 and 23 as well as a partial reduction with the rest of the compounds is observed. As expected, imatinib totally inhibits the phosphorylation of 4E-BP1 in the parental K562 line, but not in the resistant counterpart.

f. Demonstration of the Cathepsin-B Activity and the Activation of Cathepsin-L:

i) Measurement of Cathepsin-B:

FIG. 18 shows the cathepsin-B activity in U/mg of protein (y-axis) when imatinib-sensitive K562 cells (white bars) or imatinib-resistant ImaR cells (black bars) are stimulated for 24 hours with imatinib (3 µM), AICAR (0.01 mM and 1 mM), or with compounds 82 (2.5 µM), 112 (2.5 µM) or with compounds 15 (10 µM), 23 (10 µM) or 191 (10 µM). The cells are lyzed and 5 µg of proteins are placed in the presence of z-RR-AMC in a 96-well plate. The fluorescence emission at 460 nm resulting from the release of AMC is then recorded.

Figure 19:
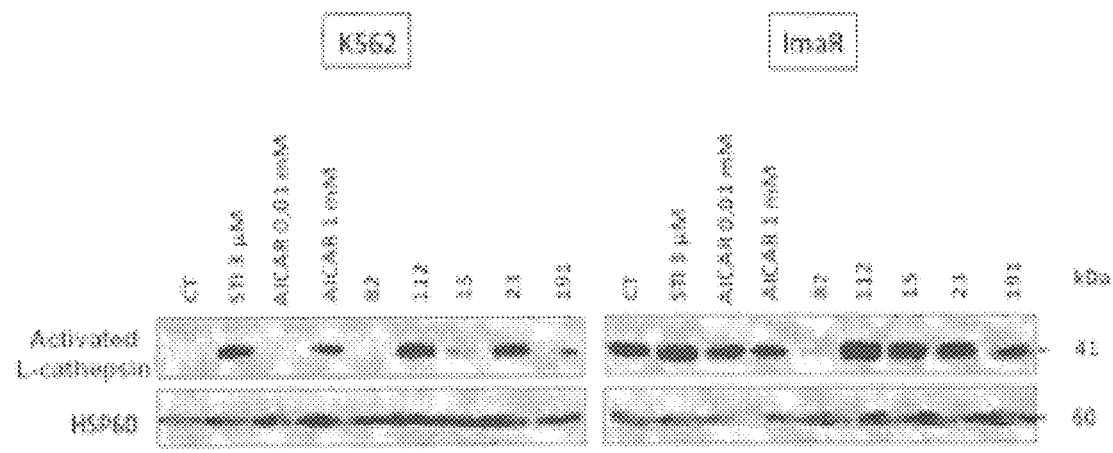
Figure 20:
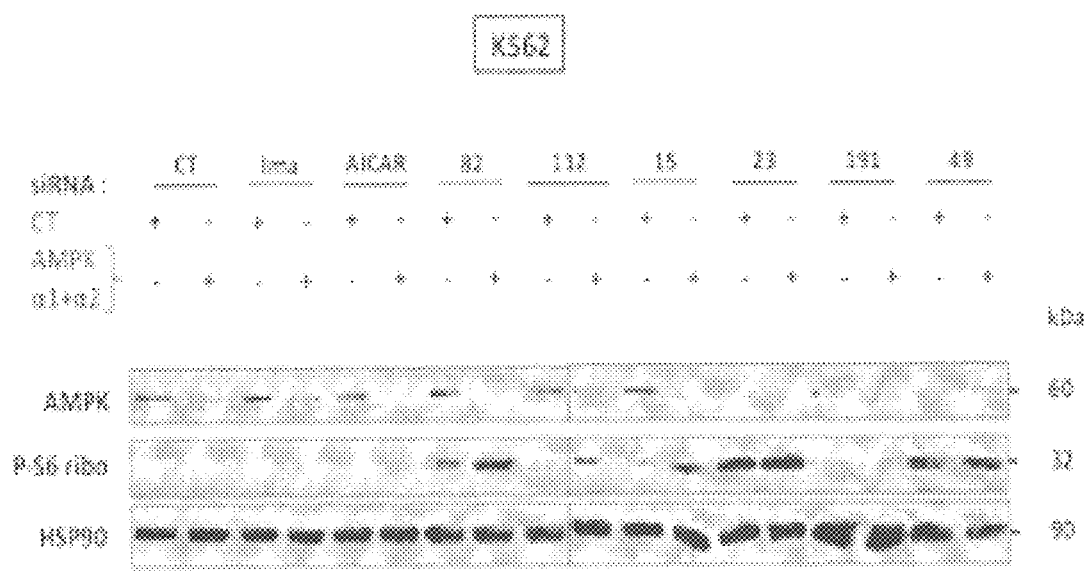

The results concerning the accumulation of p62 and LC3-II proteins led to the study of the activity of cathepsin-B then the activation cathepsin-L, effector lysosomal enzymes that are effectors of the autophagy occurring in the digestion of the contents of autophagolysosomes. Also, as shown in FIG. 18, an increase in the cathepsin-B activity by a factor of around 2 (compounds 82, 191) or greater than 3 (compounds 112, 15, 23) during treatments with AICAR (1 mM) or compounds 82, 112, 15, 23, 191 is observed, similarly in the two types of clones each time.

ii) Demonstration of the Activation of Cathepsin-L:

FIG. 19 shows a western blot analysis of the activation of cathepsin-L. The K562 and ImaR cells are stimulated for 24 hours with imatinib (3 µM), AICAR (0.01 mM and 1 mM), compounds 82 (2.5 µM), 112 (2.5 µM) or compounds 15 (10 µM), 23 (10 µM) and 191 (10 µM). The cells are lyzed and 30 µg of proteins are separated by SDS-PAGE (13% polyacrylamide gel) and analyzed by western blot with an antibody specific to cathepsin-L.

The immunoblot concerning the activation of cathepsin-L shown in FIG. 19 confirms the observations made during the measurements of cathepsin-B, since the accumulation of the activated form of cathepsin-L in the K562 clones is noted. Interestingly, cathepsin-L is not activated in the ImaR clone and does not therefore appear to be involved in the lysis of the contents of autophagosomes in this clone.

Conclusion:

According to the results shown in examples 1a to 1g above, the compounds according to the invention appear to have an anticancer activity on both imatinib-sensitive and imatinib-resistant leukemic K562 cell lines. Among these 16 compounds, the 7 compounds that are most effective after the cell viability experiments have particularly interesting characteristics and appear to be 50 to 500 times more powerful than AICAR. Also, certain compounds appear to induce autophagy alone (82, 86, 191), apoptosis alone (112), or a combination of the two types of mechanisms (15, 23, 49). However, all of these 7 compounds have, as a common mechanism of action, inhibition of the mTOR pathway shown by dephosphorylation of all of the protein substrates (FIGS. 16 and 17) and blockage of the cell cycle in phase G2/M (FIGS. 9, 10 and 11). It is also interesting to note that the apoptosis induced by compounds 112, 15, 23 and 49 is essentially relayed by the intrinsic pathway requiring mitochondrial permeabilization and activation of caspase-9.

Example 2

Thirteen new compounds, analogs of AICAR (acadesine), were evaluated on CML (chronic myeloid leukemia) lines sensitive (K562) to imatinib. These 13 compounds are presented in table 2 below.

TABLE 2

| Molecule code | Chemical formula of the molecule | Chemical name of the molecule |
|---|---|---|
| 20 | | 1'-(4-methoxycarbonyl-5-(2-furyl)-[1,2,3]-triazol-1-yl)-β-D-ribofuranose |

TABLE 2-continued

| Molecule code | Chemical formula of the molecule | Chemical name of the molecule |
|---|---|---|
| 21 | | 1'-(4-methoxycarbonyl-5-iodo-[1,2,3]-triazol-1-yl)-β-D-ribofuranose |
| 22 | | 1'-(4-carbamoyl-5-iodo-[1,2,3]-triazol-1-yl)-β-D-ribofuranose |
| 23 | | 1'-(4-carbamoyl-5-chloro-[1,2,3]-triazol-1-yl)-β-D-ribofuranose |
| 24 | | 1'-(4-phenyl-5-iodo-[1,2,3]-triazol-1-yl)-β-D-ribofuranose |
| 25 | | 1'-(4-ethoxycarbonyl-5-(2-furoyl)-[1,2,3]-triazol-1-yl)-β-D-ribofuranose |
| 26 | | 1'-(4-ethoxycarbonyl-5-(2-thienoyl)-[1,2,3]-triazol-1-yl)-β-D-ribofuranose |
| 27 | | 1'-(4-ethoxycarbonyl-5-(p-toluoyl-[1,2,3]-triazol-1-yl)-β-D-ribofuranose |
| 28 | | 1'-(4-carbamoyl-5-ethynyl-[1,2,3]-triazol-1-yl)-β-D-ribofuranose |

TABLE 2-continued

Figure 21:
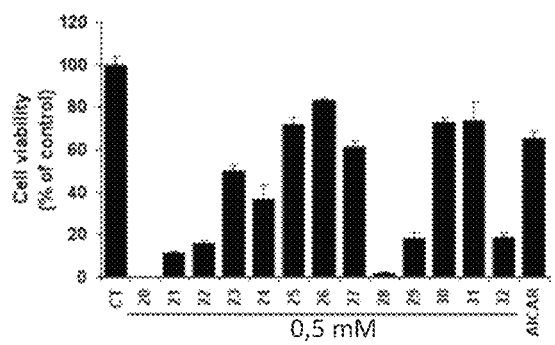
FIGS. 21 to 23 show the results of screening and dose-response studies of compounds according to the invention on CML (chronic myeloid leukemia) lines sensitive (K562) to imatinib.

| Molecule code | Chemical formula of the molecule | Chemical name of the molecule |
|---|---|---|
| 29 | | 1'-(4-methoxycarbonyl-5-ethynyl-[1,2,3]-triazol-1-yl)-β-D-ribofuranose |
| 30 | | 1'-(4-ethoxycarbonyl-5-heptanoyl-[1,2,3]-triazol-1-yl)-2',3',5'-tri-O-acetyl-β-D-ribofuranose |
| 31 | | 1'-(4-ethoxycarbonyl-5-(2-furoyl)-[1,2,3]-triazol-1-yl)-2',3',5'-tri-O-acetyl-β-D-ribofuranose |
| 32 | | 1'-(4-ethoxycarbonyl-5-p-toluoyl-[1,2,3]-triazol-1-yl)-2',3',5'-tri-O-acetyl-β-D-ribofuranose | a. Measurement of the Cell Viability of 13 Compounds According to the Invention:

To screen the 13 compounds according to the invention, the metabolic activity of the K562 cells is studied after 48 hours of treatment with 0.5 mM (effective dose of AICAR) of these different compounds. FIG. 21 shows the percentage of imatinib-sensitive K562 cells (K562) viable after stimulation or not for 48 hours with AICAR or one of the 13 compounds according to the invention (0.5 mM) described in table 1 above in a 96-well plate. After the addition of XTT reagent, the absorbance is measured at 490 nm.

The results obtained show that, among these 13 compounds, 13 compounds induce, after 48 hours of stimulation, a reduction in cell viability. This reduction in cell viability is greater than the positive control. It is also greater than or comparable to the imatinib or AICAR compound. Thus, these 13 compounds appear to be interesting candidates for active principles intended for the treatment of CML.

Figure 22:
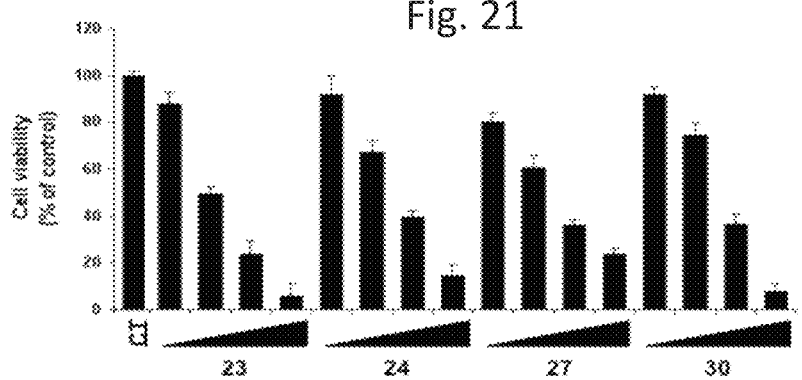
Figure 23:
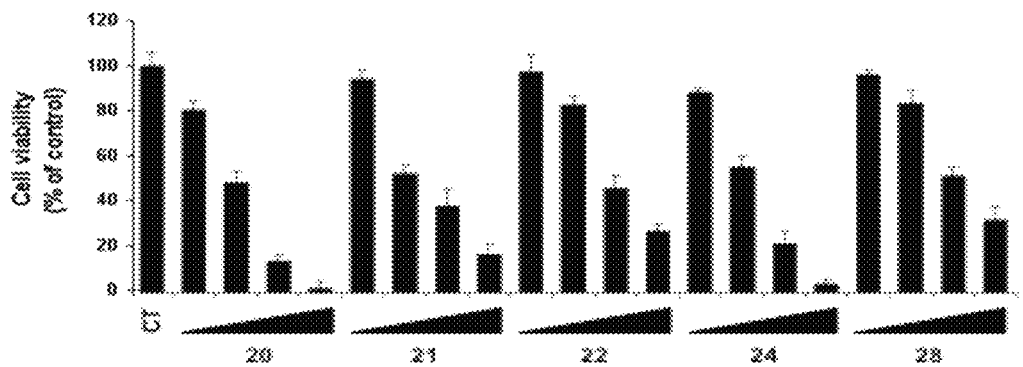

In addition, among these 13 compounds, 6 compounds (20, 21, 22, 28, 29 and 32) induce, after 48 hours of stimulation, a significant reduction in cell viability. Indeed, the percentage of viable cells changes, after 48 hours of treatment, to values below 20%.

b. Dose-Response Experiments for 15 Compounds According to the Invention:

FIGS. 22 and 23 show dose-response experiments on K562 cells exposed for 48 hours to increasing doses (5, 10, 25 and 50 μM) of one of the 9 compounds chosen from compounds 23, 24, 27, 30, 20, 21, 22, 24 and 25.

The histograms of FIGS. 22 and 23 show the dose-response effect of each of these 9 compounds. After adding XTT reagent, the absorbance is measured at 490 nm.

The results shown in FIGS. 22 and 23 show a dose-dependent reduction in the number of viable cells for the 9 compounds after 48 hours of stimulation. These 9 compounds are found to be particularly effective on the K562 cells at concentrations of 50 μM. The IC50 is on the order of 5 μM for compounds 20, 21, 23, 24 and 30, and around 10 μM for compounds 22, 27, 28 and 61.

Example 3

Procedure Concerning the Synthesis of Compounds According to the Invention

Trimethylsilyl, then $BF_3$-$Et_2O$, are added one drop at a time to a solution of 1',2',3',5'-tetraacetate-β-D-ribose in 50 ml of dichloromethane. The reaction medium is left at room temperature for around 1 hour, then is washed with a saturated aqueous sodium hydrogen carbonate solution. The organic phase is dried on magnesium sulfate, then the solvent is evaporated under reduced pressure. The oil obtained is purified on a silica column. Compound 1 is obtained in the form of a colorless oil:

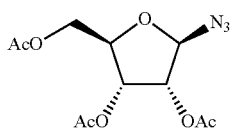

1

Sodium azide is added to a solution of 4-methylbenzyl bromide in 50 ml of dimethyl-formamide. The reaction medium is left at room temperature for around 2 hours, the solvent is evaporated under reduced pressure and 100 ml of dichloromethane are added. The organic phase is washed 2 times with water, then with a saturated NaCl solution, dried on magnesium sulfate, then the solvent is evaporated under reduced pressure. The oil obtained is purified on a silica column. Compound 2 is obtained in the form of a colorless oil.

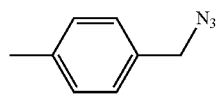

2

Ethyl propiolate, copper cyanide (I), 35% oxygenated water and N,N-diisopropylethylamine are added in succession to a solution of azide 1 in 5 ml of tetrahydrofuran (or 2-methyl-tetrahydrofuran) at 0° C. The reaction medium is stirred at 0° C. for around 10 minutes, then brought to room temperature. After the end of the reaction, the reaction medium is filtered on a celite bed and the solvent is evaporated under reduced pressure. The raw material obtained is purified on a silica column. Compound 3 is obtained in the form of a brown oil. In the optimized method, 2-methyl-tetrahydrofuran and bromo-tris(triphenylphosphine) CuBr (PPh$_3$)$_3$ are used.

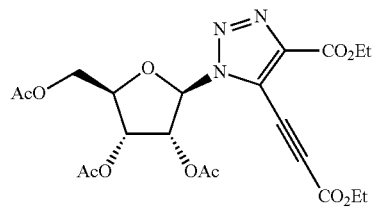

3

Ethyl propiolate, copper cyanide (I), 35% oxygenated water and N,N-diisopropylethylamine are added in succession to a solution of azide 2 in 5 ml of tetrahydrofuran at 0° C. The reaction medium is stirred at 0° C. for around 10 minutes, then brought to room temperature. After the end of the reaction, the reaction medium is filtered on a celite bed and the solvent is evaporated under reduced pressure. The raw material obtained is purified on a silica column. Compound 4 is obtained in the form of a yellow solid. In the optimized method, 2-methyl-tetrahydrofuran and bromo-tris(triphenylphosphine) CuBr(PPh$_3$)$_3$ are used.

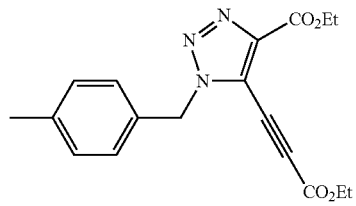 [SMILES: CCOC(=O)C#Cc1c(C(=O)OCC)nnn1Cc1ccc(C)cc1]

4

Ethyl propiolate, I$_2$, cerium ammonium nitrate, copper iodide (I) and N,N-diisopropylethylamine are added to a solution of azide 1 in 20 ml of tetrahydrofuran (or 2-methyl-tetrahydrofuran). The reaction medium is left at room temperature for around 15 minutes, then filtered on a celite bed. The solvent is evaporated under reduced pressure and the dark oil obtained is purified on a silica column. Compound 5 is obtained in the form of a brown solid. In the optimized method, 2-methyl-tetrahydrofuran is used instead of THF.

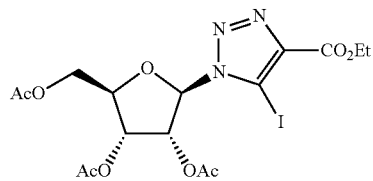

5

Ethyl propiolate, N-chlorosuccinimide, copper chloride (I) and N,N-diisopropylethylamine are added to a solution of azide 1 in 10 ml of dichloromethane. The reaction medium is left at room temperature for 2 hours, then is filtered on a celite bed. The solvent is evaporated under reduced pressure and the oil obtained is purified on a silica column. Compound 6 is obtained in the form of an oil.

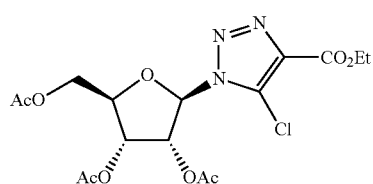

6

Ethyl propiolate, p-toluoyl chloride, copper iodide (I) and N,N'-diisopropylethylamine are added to a solution of azide 1 in 5 ml of tetrahydrofuran (or 2-methyl-tetrahydrofuran). The reaction medium is left at room temperature for 30 minutes, then filtered on a celite bed. The solvent is evaporated under reduced pressure and the oil obtained is purified on a silica column. Compound 7 is obtained in the form of an oil.

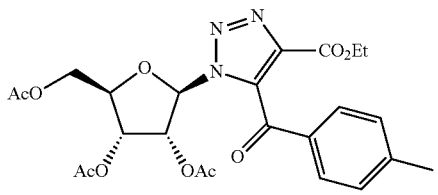

7

Ethynyltriethylsilane, Pd(PPh$_3$)$_2$Cl$_2$, copper iodide (I) and triethylamine are added to a solution of 5 in 20 mL of toluene. The reaction medium is heated at 60° C. for 90 minutes, then filtered on a celite bed and the solvent is evaporated under reduced pressure. The oil obtained is purified on a silica column. Compound 8 is obtained in the form of an oil.

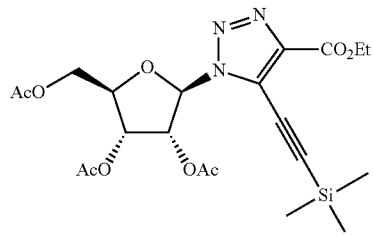

8

A solution of 8 in 40 mL of methanol is placed in an ice-water bath. Ammonia is bubbled for several seconds, then the reaction medium is left to return to room temperature. After one night, the solvent is evaporated under reduced pressure and the oil obtained is purified on a silica column. Compounds 9 and 10 are obtained in the form of foams.

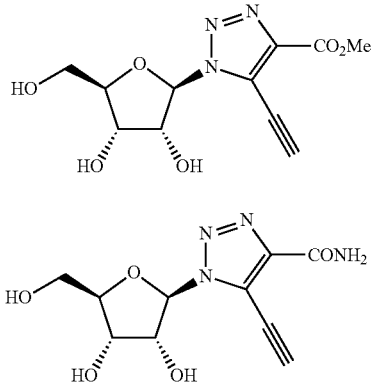

2 (tributylstannyl)thiophene, Pd(PPh$_3$)$_2$Cl$_2$, copper iodide (I) and triethylamine are added to a solution of 5 in 10 ml of toluene. The reaction medium is heated at 80° C. for around 3 hours, filtered on a celite bed, then the solvent is evaporated under reduced pressure. The oil obtained is purified on a silica column. Compound 11 is obtained in the form of a brown oil.

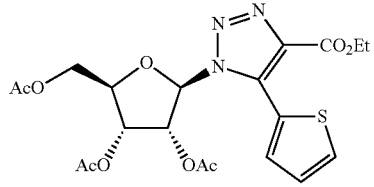

Sodium carbonate is added to a solution of 11 in 20 ml of ethanol. The reaction medium is stirred at room temperature for one hour, then the solvent is evaporated under reduced pressure and the raw material obtained is purified on a silica column. Compound 12 is obtained in the form of a yellow oil.

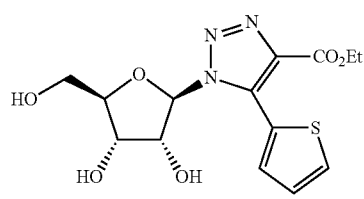

A solution of 11 in 30 ml of methanol is placed in an ice-water bath. Ammonia gas is bubbled for several seconds, then the reaction medium is left to return to room temperature. After one night, the solvent is evaporated under reduced pressure and the oil obtained is purified on a silica column. Compound 13 is obtained in the form of a yellow oil.

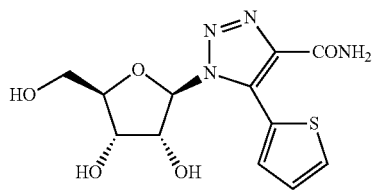

Example 4

Procedure Concerning the Synthesis of Compounds According to the Invention

Sodium carbonate is added to a solution of azide 1 (1-azideo-2,3',4'-tri-O-acetyl ribose) in 20 ml of methanol. The reaction medium is stirred at room temperature for one hour, then the solvent is evaporated under reduced pressure and the raw material obtained is purified on a silica column. Compound 14 is obtained in the form of a colorless oil.

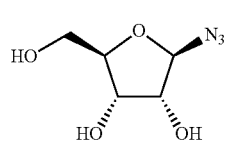

2,2-dimethoxypropane, then boron trifluoride etherate are added one drop at a time in succession to a solution of azide 14 in 20 ml of acetone at 0° C. The mixture is stirred at 0° C. for 30 minutes, then at room temperature for one hour. The reaction medium is poured into a triethylamine solution (10%) in 20 ml of acetone, at 0° C. After 10 minutes under stirring, the neutralized solution is evaporated and the yellow oil obtained is purified on a silica column (eluent CH$_2$Cl$_2$-MeOH: 98-2). Compound 15 is obtained in the form of a colorless oil.

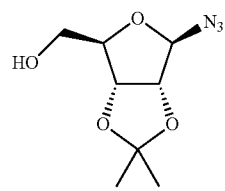

Ethyl propiolate, copper cyanide (I), 35% oxygenated water and N,N-diisopropylethylamine are added in succession to a solution of azide 15 in 5 ml of tetrahydrofuran (or 2-methyl-tetrahydrofuran) at 0° C. The reaction medium is stirred at 0° C. for around 10 minutes, then brought to room temperature. After the end of the reaction, the reaction medium is filtered on a celite bed and the solvent is evaporated under reduced pressure. The raw material obtained is purified on a silica column (eluent:cyclohexane-AcOEt:7-3). Compound 16 is obtained in the form of an oil. In the optimized method, 2 methyl-tetrahydrofuran and bromo-tris-(triphenylphosphine) CuBr(PPh$_3$)$_3$ are used.

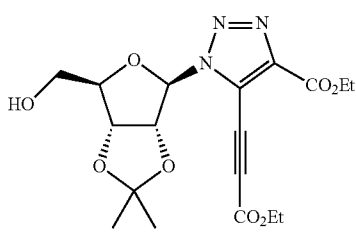

16

4-dimethylaminopyridine (DMAP) is added to a solution of 16 in 2 ml of acetic anhydride. The reaction medium is stirred at room temperature for two hours. After the end of the reaction, the solvent is evaporated under reduced pressure. The raw material obtained is purified on a silica column (eluent:cyclohexane-AcOEt:9-1). Compound 17 is obtained in the form of an oil.

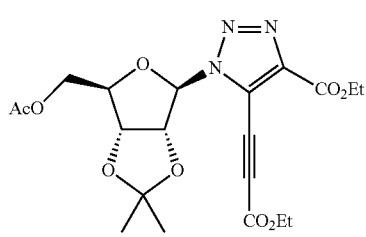

17

Ethyl propiolate, $I_2$, cerium ammonium nitrate, copper iodide (I) and N,N-diisopropylethylamine are added to a solution of azide 15 in 20 ml of tetrahydrofuran (or 2-methyltetrahydrofuran). The reaction medium is left at room temperature for around 20 minutes, then filtered on a celite bed. The solvent is evaporated under reduced pressure and the dark oil obtained is purified on a silica column (eluent:cyclohexane-AcOEt:8-2). Compound 18 is obtained in the form of a brown solid.

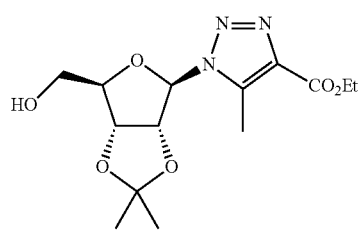

18 a—(Stille coupling): 2-(tributylstannyl)thiophene, Pd(PPh$_3$)$_4$ and copper iodide (I) are added to a solution of 18 in 10 ml of toluene. The reaction medium is heated at 80° C. for 2 hours, filtered on a celite bed, then the solvent is evaporated under reduced pressure. The oil obtained is purified on a silica column (eluent:cyclohexane-AcOEt:8-2). Compound 19 is obtained in the form of an oil.

b—(Suzuki coupling): 0.5 ml of a Na$_2$CO$_3$ (1M) solution, then thiophene-2-boronic acid are added to a solution of compound 18 in dioxane (2 ml). The mixture is then degassed and placed under argon, then the catalyst Pd(PPh$_3$)$_4$ is added. It is heated at 85° C. under stirring for 4 hours. The reaction medium is neutralized with 10 ml of HCl (1M), and 20 ml of ethyl acetate are added. The organic phase is then extracted with an NaCl solution and evaporated under reduced pressure. The raw residue is purified on a silica column (eluent: cyclohexane-AcOEt:8-2). Compound 19 is obtained in the form of an oil.

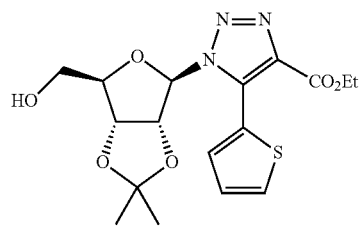

19

4-dimethylaminopyridine (DMAP) is added to a solution of 19 in 2 ml of acetic anhydride. The reaction medium is stirred at room temperature for two hours. After the end of the reaction, the solvent is evaporated under reduced pressure. The raw material obtained is purified on a silica column (eluent:cyclohexane-AcOEt:9-1). Compound 20 is obtained in the form of an oil.

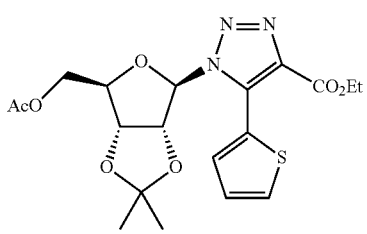

20

Toluoyl chloride is added to a solution of 1'-acetyl deoxyribose in 60 ml of pyridine. The reaction medium is left at room temperature for 30 minutes. After extraction with dichloromethane, drying on magnesium sulfate and filtration, the solvent is evaporated under reduced pressure and the oil obtained is purified on a silica column (eluent:cyclohexane-AcOEt:8-2). Compound 21 is obtained in the form of a yellow oil that solidifies to give a beige solid.

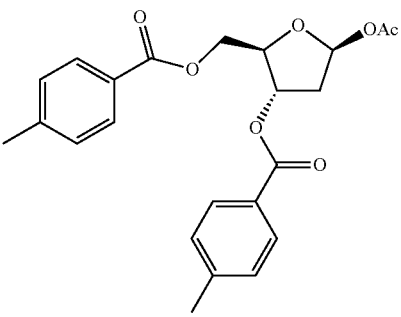

21

Trimethylsilyl azide, then BF$_3$-Et$_2$O are added one drop at a time to a solution of 21 in 50 ml of dichloromethane. The reaction medium is left at room temperature for around 3 hours, then is washed with a saturated aqueous sodium hydrogen carbonate solution. The organic phase is dried on magnesium sulfate, then the solvent is evaporated under reduced pressure. The oil obtained is purified on a silica column (eluent:cyclohexane-AcOEt:9-1). Compound 22 is obtained in the form of a colorless oil.

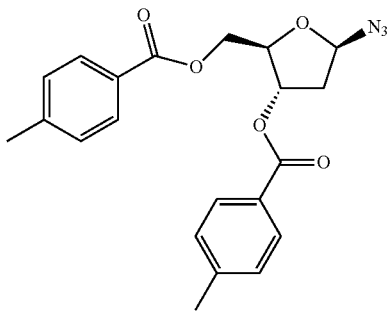

22

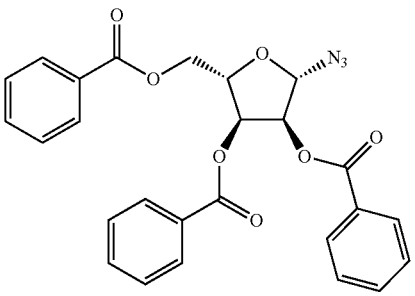

24

Ethyl propiolate, copper cyanide (I), 35% oxygenated water and N,N-diisopropylethylamine are added in succession to a solution of azide 22 in 5 ml of tetrahydrofuran at 0° C. The reaction medium is stirred at 0° C. for around 10 minutes, then brought to room temperature. After the end of the reaction, the reaction medium is filtered on a celite bed and the solvent is evaporated under reduced pressure. The raw material obtained is purified on a silica column (eluent; cyclohexane-AcOEt:8-2). Compound 23 is obtained in the form of a solid. In the optimized method, 2-methyl-tetrahydrofuran and bromo-tris-(triphenylphosphine) CuBr(PPh$_3$)$_3$ are used.

Ethyl propiolate, copper cyanide (i), 35% oxygenated water and N,N-diisopropylethylamine are added in succession to a solution of azide 24 in 5 ml of tetrahydrofuran at 0° C. The reaction medium is stirred at 0° C. for around 10 minutes, then brought to room temperature. After the end of the reaction, the reaction medium is filtered on a celite bed and the solvent is evaporated under reduced pressure. The raw material obtained is purified on a silica column (eluent:cyclohexane-AcOEt:8-2). Compound 25 is obtained in the form of a brown solid. In the optimized method, 2-methyl-tetrahydrofuran and bromo-tris-(triphenylphosphine) CuBr(PPh$_3$)$_3$ are used.

23

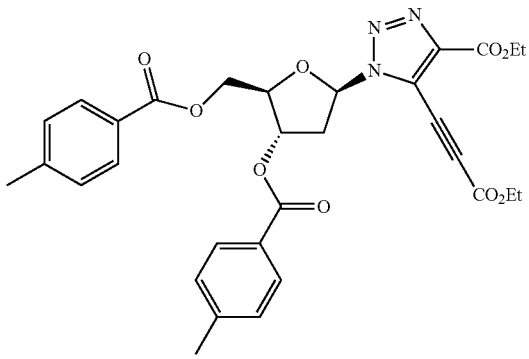

25

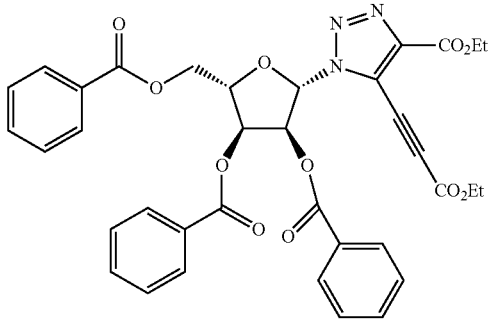

Trimethylsilyl azide, then trifluoride borane etherate are added one drop at a time to a solution of 1,2,3,5-tetra-O-benzoyl-β-L-ribofuranose in 100 ml of dichloromethane. The reaction medium is left at room temperature for 2 hours, then washed with a saturated aqueous sodium hydrogen carbonate solution. The organic phase is dried on magnesium sulfate, filtered, then the solvent is evaporated under reduced pressure. The oil obtained is purified on a silica column (eluent: cyclohexane-AcOEt:9-1). Compound 24 is obtained in the form of a white solid.

Example 5

Analysis of the Efficacy of Five Compounds According to the Invention on Different Hematopoietic Lines and Solid Cancers The efficacy and the LD50's (median lethal doses) of five compounds according to the invention, presented in table 3 below, were determined on 6 malignant blood disease cell lines.

TABLE 3

| Molecule code | Chemical formula of the molecule | Chemical name of the molecule |
| --- | --- | --- |
| 82 |  | 1'-(4-ethoxycarbonyl-5-(2-thienyl)-[1,2,3]-triazol-1-yl)-2',3',5'-tri-O-acetyl-β-D-ribofuranose |

TABLE 3-continued

| Molecule code | Chemical formula of the molecule | Chemical name of the molecule |
|---|---|---|
| 86 | | 1'-(4-ethoxycarbonyl-5-phenyl-[1,2,3]-triazol-1-yl)-2',3',5'-tri-O-acetyl-β-D-ribofuranose |
| 112 | | 1-(4-methoylbenzyl)-4-ethoxycarbonyl-5-ethyl propiolate-1,2,3-triazole |
| 196 | | 1'-(4-ethoxycarbonyl-5-ethyl propiolate-[1,2,3]-triazol-1-yl)-2',3',4',6'-tetra-O-acetyl-β-D-glucopyranose |
| 236 | | 1'-(4-ethoxycarbonyl-5-(2-thienyl)-[1,2,3]-triazol-1-yl)-2',3'-O-isopropylidene-β-D-ribofuranose |

The results of this study are presented in table 4 below.

TABLE 4

| Lines | Compound 49 | Compound 82 | Compound 86 | Compound 112 | Compound 196 | Compound 236 |
|---|---|---|---|---|---|---|
| MEC-1 (chronic lymphoblastic B-cell leukemia) | 0.2 | 0.75 | 2.5 | 1 | 0.1 | 1 |
| J16 (T-cell lymphoma) | 2.5 | 1.5 | 5 | 2.5 | 0.75 | 2 |
| 8866 (lymphoblastic B-cell leukemia) | 3 | 1.5 | 4 | 1.5 | 3 | 2.5 |
| U 937 (monocyte lymphoma) | 0.5 | 1 | 2.5 | 2 | 0.1 | 2 |
| RAJI (Burkitt) | >10 | 2.5 | 10 | 10 | >10 | 4 |
| 8226 (myeloma) | 1.5 | 2.5 | 2.5 | 1.5 | 0.5 | 1.5 |

Similarly, the efficacy and the LD50's (median lethal doses) of these five compounds presented in table 3 above were determined on nine solid cancer cell lines of different origins. The results of this study are presented in table 5 below.

TABLE 5

| Lines | Compound 49 | Compound 82 | Compound 86 | Compound 112 | Compound 196 | Compound 236 |
|---|---|---|---|---|---|---|
| HCT8R (colon cancer) | >10 | 3.5 | >10 | 10 | >10 | 4 |
| MDAM 453 (breast cancer) | >10 | 1 | 5 | >10 | >10 | 1 |
| A 375 (melanoma) | 7.5 | 2 | 5 | 7.5 | 10 | 2 |
| SHSY-5Y (neuroblastoma) | >10 | 1.5 | 3 | >10 | >10 | 0.5 |
| Pc3 (prostate cancer) | >10 | 3 | 10 | >10 | >10 | 5 |
| NCIH 226 (lung cancer) | >10 | 2.5 | 7.5 | 10 | >10 | 4 |
| MEWO (melanoma, p53 mutated) | >10 | 1.5 | 7.5 | >10 | >10 | 3 |
| SF 278 (glioblastoma) | 10 | 1.5 | 2.5 | 10 | >10 | 2.5 |
| HEK (kidney cancer) | >10 | 1.5 | 6 | >10 | >10 | 2.5 |

Thus, the results presented in table 4 above show that all of the molecules tested have an efficacy on malignant blood diseases. The most effective derivatives are molecules 82, 196 and 236.

In table 5, it was noted that the molecules are generally more effective on malignant blood diseases than on solid cancers. However, derivatives 82 and 236, with very similar structures, also show significant efficacy on all of the cancers tested.

Example 6

"In Vivo" Analysis of the Efficacy of Derivatives 86, 196 and 236

The three compounds (86, 196 and 236) were tested at 1 mg/kg on the tumor growth of imatinib-resistant CML K562 cells in athymic nude mice. The tumors of the mice of each group are weighed on the day of sacrifice, and the sum of these masses constitutes a tumor growth index. This index is expressed as a percentage with respect to the growth of the control group (second line).

The results of this "in vivo" analysis are presented in table 6 below.

TABLE 6

|  | Control | Compound 86 | Compound 196 | Compound 236 |
|---|---|---|---|---|
| Mass of tumors at the end of the campaign (% vs. control) | 100 | 69.6 | 42 | 60.3 |
| Mean weight of the mice on the day of sacrifice | 18.63 | 18.43 | 20.5 | 20.14 |

As shown in table 6 above, all of the molecules showed efficacy on the development of the tumor mass. It is also possible to note that compound 196 appears to be the most effective, with inhibition of around 60% of the tumor mass, followed by compound 236 and finally 86.

It is also noted that the mice treated do not have any sign of alteration of their general state after the treatments received.

An index of the satisfactory state of the mice is the mean of the weight of each group presented in the third line of the table.

The invention claimed is:

1. A method for treating cancer, the method comprising:
administering to a patient in need thereof a compound of the general formula I in a suitable medium for administration to the patient; wherein general formula I is

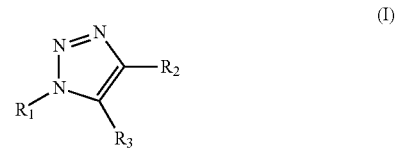

and wherein:

$R_1$ is chosen from:

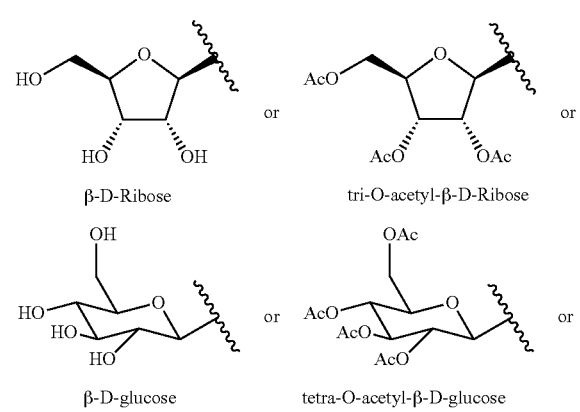

-continued

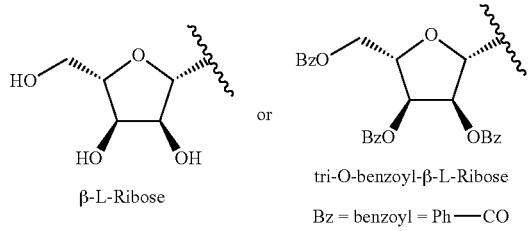

β-L-Ribose tri-O-benzoyl-β-L-Ribose

Bz = benzoyl = Ph—CO

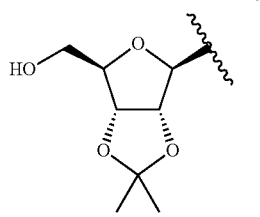

2′,3′-isopropylidene-β-D-Ribose

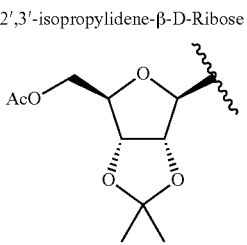

5′-O-acetyl-2′,3′-isopropylidene-β-D-Ribose

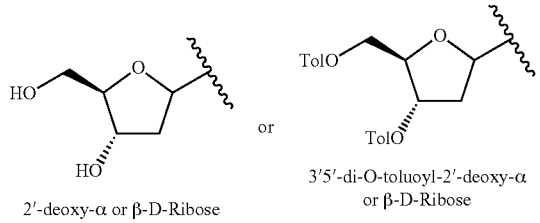

2′-deoxy-α or β-D-Ribose

3′5′-di-O-toluoyl-2′-deoxy-α or β-D-Ribose

Tol = 4-Me—Ph—CO

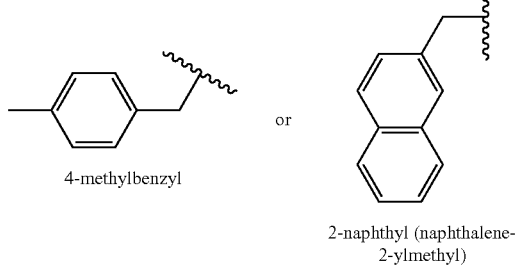

4-methylbenzyl 2-naphthyl (naphthalene-2-ylmethyl)

$R_2$ is chosen from:
- a —$CONH_2$, —CONHMe, —CONHEt, —CON$(Me)_2$, —CON$(Et)_2$ amide group,
- a —$CO_2H$, $CO_2Me$, $CO_2Et$ acid or ester group, a —CN, —$C(NH_2)NH$, —C(NHMe)NH, —C(NHEt)NH cyano or amidine group,
- a phenyl group optionally substituted by a halogen chosen from Cl, Br, I and F,
- a thiophene group,
- a linear or branched carbon chain having 3 to 10 carbon atoms, or
- a methoxynaphthalene group; and $R_3$ is chosen from:
- a halogen group,
- a furan or —CO-furan group,
- a thiophene or —CO-thiophene or —C≡C-thiophene group,
- a toluoyl group,
- an acetylene group,
- a —CO—$(CH_2)_n$—$CH_3$ group, with n between 2 and 9,
- a phenyl or —C≡C-phenyl group, optionally substituted by a halogen,
- a —C≡C—$CO_2Me$, —C≡C—$CO_2Et$, —C≡C—$CONH_2$ group,
- a —C≡C—$(CH_2)_6CH_3$, group, or
- a —C≡C-2-methoxynaphthalene group;

the racemates, enantiomers, diastereoisomers thereof and mixtures thereof, the tautomers thereof and the pharmaceutically acceptable salts thereof.

2. The method of claim 1, wherein the cancer is selected from the group consisting of solid tumors, malignant blood diseases, chronic myeloid leukemia (CML), tyrosine kinase inhibitor-resistant cancers, and tyrosine kinase inhibitor-resistant chronic myeloid leukemias.

3. The method of claim 1, wherein:
$R_2$ is chosen from —$CONH_2$, —$CO_2Me$, —$CO_2Et$, phenyl, thiophene, —$(CH_2)_6CH_3$, p-fluoro-phenyl or 2-methoxynaphthalene; and
$R_3$ is chosen from I, Cl, furan, CO-furan, CO-thiophene, acetylene, CO—$(CH_2)_5$—$CH_3$, toluoyl, —C≡C—$CO_2Et$, thiophene, phenyl, —C≡C-phenyl, —C≡C-thiophene, —C≡C—$(CH_2)_6CH_3$, —C≡C-(p-fluoro-phenyl), or —C≡C-2-methoxynaphthalene;
the racemates, enantiomers, diastereoisomers thereof and mixtures thereof, the tautomers thereof and the pharmaceutically acceptable salts thereof.

4. The method of claim 3, wherein $R_1$ is:
when $R_1$ is a β-D-ribose, then:
$R_2$=$CONH_2$ and $R_3$=I, Cl, CO-Furan, CO-thiophene, toluoyl or acetylene;
or
$R_2$=$CO_2Me$ and $R_3$=I, furan or acetylene;
or
$R_2$=phenyl and $R_3$=I;
when $R_1$ is a tri-O-acetyl-β-D-ribose group, then:
$R_2$=$CO_2Et$ and $R_3$=Cl, CO—$(CH_2)_5$—$CH_3$, CO-furan, toluoyl, —C≡C—$CO_2Et$, thiophene or phenyl;
or
$R_2$=phenyl and $R_3$=—C≡C-phenyl;
or
$R_2$=thiophene and $R_3$=—C≡C-thiophene;
or
$R_2$=$(CH_2)_6CH_3$ and $R_3$=—C≡C—$(CH_2)_6CH_3$;
or
$R_2$=p-fluoro-phenyl and $R_3$=—C≡C-p-fluoro-phenyl;
or
$R_2$=2-methoxynaphthalene and
$R_3$=—C≡C-2-methoxynaphthalene;
when $R_1$ is a tetra-O-acetyl-β-D-glucose group, then $R_2$=$CO_2Et$ and $R_3$=I or —C≡C—$CO_2Et$;
when $R_1$ is a tri-O-benzoyl-β-L-ribose group, then $R_2$=$CO_2Et$ and $R_3$=—C≡C—$CO_2Et$;
when $R_1$ is a 2′,3′-isopropylidene-β-D-ribose group, then $R_2$=$CO_2Et$ and $R_3$=—C≡C—$CO_2Et$ or thiophene;
when $R_1$=5′-O-acetyl-2′,3′-isopropylidene-β-D-ribose, then $R_2$=$CO_2Et$ and $R_3$=—C≡C—$CO_2Et$ or thiophene;

when R$_1$ is a 3',5'-di-O-toluoyl-2'-deoxy-β-D-ribose group, then R$_2$=CO$_2$Et and R$_3$=—C≡C—CO$_2$Et;
when R$_1$ is a 4-methylbenzyl group, then:
R$_2$=CO$_2$Et and R$_3$=—C≡C—CO$_2$Et;
or
R$_2$-phenyl and R$_3$=—C≡C-phenyl;
when R$_1$ is a 2-naphthyl (naphthalene-2-ylmethyl) group, then:
R$_2$=CO$_2$Et and R$_3$=I;
or
R$_2$=CO$_2$Et and R$_3$=—C≡C—CO$_2$Et;
or
R$_2$=Phenyl and R$_3$=—C≡C-phenyl;
the racemates, enantiomers, diastereoisomers thereof and mixtures thereof, the tautomers thereof and the pharmaceutically acceptable salts thereof.

5. The method of claim 1, wherein R$_1$ is:

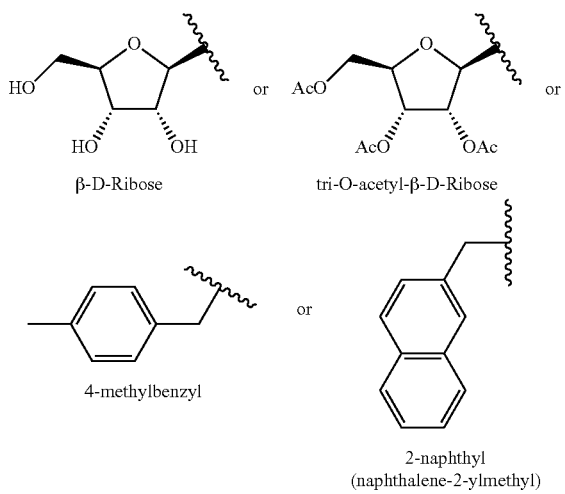

β-D-Ribose    tri-O-acetyl-β-D-Ribose 4-methylbenzyl 2-naphthyl
(naphthalene-2-ylmethyl)

and
when R$_1$ is a 13-D-ribose group, then:
R$_2$=CONH$_2$ and R$_3$=Cl, CO-furan, CO-thiophene or toluoyl;
or
R$_2$=CO$_2$Me and R$_3$=I or acetylene;
or
R$_2$=phenyl and R$_3$=I;
when R$_1$ is a tri-O-acetyl-β-D-ribose group, then:
R$_2$=CO$_2$Et and R$_3$=CO—(CH$_2$)$_5$—CH$_3$, CO-furan, toluoyl, —C≡C—CO$_2$Et, thiophene or phenyl;
or
R$_2$=phenyl and R$_3$=—C≡C-phenyl;
or
R$_2$=thiophene and R$_3$=—C≡C-thiophene;
or
R$_2$=(CH$_2$)$_6$CH$_3$ and R$_3$=—C≡C—(CH$_2$)$_6$CH$_3$;
or
R$_2$=p-fluoro-phenyl and R$_3$=—C≡C-p-fluoro-phenyl;
or
R$_2$=2-methoxynaphthalene and
R$_3$=—C≡C-2-methoxynaphthalene;
when R$_1$ is a 4-methylbenzyl group, then:
R$_2$=CO$_2$Et and R$_3$=—C≡C—CO$_2$Et;
or
R$_2$=phenyl and R$_3$=—C≡C-phenyl;
when R$_1$ is a 2-naphthyl (naphthalene-2-yl-methyl) group, then:

R$_2$=CO$_2$Et and R$_3$=I;
or
R$_2$=CO$_2$Et and R$_3$=—C≡C—CO$_2$Et;
or
R$_2$=Phenyl and R$_3$=—C≡C-phenyl;
the racemates, enantiomers, diastereoisomers thereof and mixtures thereof, the tautomers thereof and the pharmaceutically acceptable salts thereof.

6. The method of claim 1, wherein the compound of formula (I) is selected from the group consisting of:
1'-(4-ethoxycarbonyl-5-iodo-[1,2,3]-triazol-1-yl)-2',3',5'-tri-O-acetyl-β-D-ribofuranose;
1'-(4-carbamoyl-5-iodo-[1,2,3]-triazol-1-yl)-β-D-ribofuranose;
1'-(4-methoxycarbonyl-5-ethynyl-[1,2,3]-triazol-1-yl)-β-D-ribofuranose;
1-(naphthyl-2-methyl)-4-ethoxycarbonyl-5-iodo-1,2,3-triazole;
1-(naphthyl-2-methyl)-4-ethoxycarbonyl-5-ethyl propiolate-1,2,3-triazole;
1'-(4-ethoxycarbonyl-5-ethyl propiolate-[1,2,3]-triazol-1-yl)-2',3',5'-tri-O-acetyl-β-D-ribofuranose;
1'-(4-ethoxycarbonyl-5-(2-thienyl)-[1,2,3]-triazol-1-yl)-2',3',5'-tri-O-acetyl-β-D-ribofuranose;
1'-(4-ethoxycarbonyl-5-phenyl-[1,2,3]-triazol-1-yl)-2',3',5'-tri-O-acetyl-β-ribofuranose;
1-(4-methylbenzyl)-4-ethoxycarbonyl-5-ethyl propiolate-1,2,3-triazole;
1'-(4-heptyl-5-(non-1-yn-1-yl-[1,2,3]-triazol-1-yl)-2',3',5'-tri-O-acetyl-β-D-ribofuranose;
1'-(4-ethoxycarbonyl-5-ethyl propiolate-[1,2,3]-triazol-1-yl)-2',3',5'-tri-O-benzoyl-β-L-ribofuranose;
2'-deoxy-1'-(4-ethoxycarbonyl-5-ethyl propiolate-[1,2,3]-triazol-1-yl)-3',5'-di-O-(p-toluoyl)-α-D-ribofuranose;
1'-(4-ethoxycarbonyl-5-ethyl propiolate-[1,2,3]-triazol-1-yt)-2',3',4',6'-tetra-O-acetyl-β-D-glucopyranose;
1'-(4-ethoxycarbonyl-5-ethyl propiolate-[1,2,3]-triazol-1-yl)-2',3'-O-isopropylidene-β-D-ribofuranose;
1'-(4-ethoxycarbonyl-5-ethyl propiolate-[1,2,3]-triazol-1-yl)-2',3'-O-isopropylidene-5'-O-acetyl-β-D-ribofuranose;
1'-(4-ethoxycarbonyl-5-(2-thienyl)-[1,2,3]-triazol-1-yl)-2',3'-O-isopropylidéne-β-D-ribofuranose; and
1'-(4-ethoxycarbonyl-5-(2-thienyl)-[1,2,3]-triazol-1-yl)-2',3'-O-isopropylidene-5'-O-acetyl-β-D-ribofuranose, and combinations thereof.

7. The method of claim 1, wherein the compound of formula (I) is selected from the group consisting of:
1'-(4-ethoxycarbonyl-5-(2-thienyl)-[1',2',3']-triazol-1-yl)-2',3',5'-tri-O-acetyl-β-D-ribofuranose;
1'-(4-ethoxycarbonyl-5-ethyl propiolate-[1,2,3]-triazol-1-yl)-2',3',5'-tri-O-acetyl-β-D-ribofuranose;
1'-(4-ethoxycarbonyl-5-ethyl propiolate-[1,2,3]-triazol-1-yl)-2',3'-O-isopropylidene-β-D-ribofuranose;
1'-(4-ethoxycarbonyl-5-ethyl propiolate-[1,2,3]-triazol-1-yl)-2',3'-O-isopropylidene-5'-O-acetyl-β-D-ribofuranose; and
1-(4-methylbenzyl)-4-ethoxycarbonyl-5-ethyl propiolate-1,2,3-triazole, and combinations thereof.

8. A compound selected from the group consisting of:
1'-(4-ethoxycarbonyl-5-(2-thienyl)-[1,2,3]-triazol-1-yl)-2',3',5'-tri-O-acetyl-β-D-ribofuranose;
1'-(4-ethoxycarbonyl-5-phenyl-[1,2,3]-triazol-1-yl)-2',3',5'-tri-O-acetyl-β-D-ribofuranose;
1-(4-methylbenzyl)-4-ethoxycarbonyl-5-ethyl propiolate-1,2,3-triazole;

1'-(4-ethoxycarbonyl-5-ethyl propiolate-[1,2,3]-triazol-1-yl)-2',3',4',6'-tetra-O-acetyl-β-D-glucopyranose;

1'-(4-ethoxycarbonyl-5-(2-thienyl)-[1,2,3]-triazol-1-yl)-2',3'-O-isopropylidene-β-D-ribofuranose;

1'-(4-ethoxycarbonyl-5-ethyl propiolate-[1,2,3]-triazol-1-yl)-2',3',5'-tri-O-acetyl-β-D-ribofuranose; and 1'-(4-ethoxycarbonyl-5-ethyl propiolate-[1,2,3]-triazol-1-yl)-2',3'-O-isopropylidene-β-D-ribofuranose.

9. The method of claim 1, wherein the compound of formula (I) is contained in a composition further comprising a pharmaceutically acceptable carrier.

10. The method of claim 1, further comprising administering simultaneously, separately or sequentially, to a human in need thereof at least one second active ingredient.

* * * * *